(12) United States Patent
Takiguchi

(10) Patent No.: US 8,028,582 B2
(45) Date of Patent: *Oct. 4, 2011

(54) MARKER DETECTION APPARATUS AND MARKER DETECTION METHOD

(75) Inventor: Kiyoaki Takiguchi, Kanagawa (JP)

(73) Assignee: Sony Corporation, Tokyo (JP)

( * ) Notice: Subject to any disclaimer, the term of this patent is extended or adjusted under 35 U.S.C. 154(b) by 623 days.

This patent is subject to a terminal disclaimer.

(21) Appl. No.: 11/875,380

(22) Filed: Oct. 19, 2007

(65) Prior Publication Data

US 2009/0031814 A1 Feb. 5, 2009

(30) Foreign Application Priority Data

Oct. 23, 2006 (JP) ................... 2006-287898

(51) Int. Cl.
*G01H 3/00* (2006.01)
(52) U.S. Cl. .......................................... 73/658
(58) Field of Classification Search .......... 73/584, 73/658; 356/338
See application file for complete search history.

(56) References Cited

U.S. PATENT DOCUMENTS

| | | | |
|---|---|---|---|
| 4,673,288 A * | 6/1987 | Thomas et al. ............. | 356/72 |
| 5,641,457 A | 6/1997 | Vardanega et al. | |
| 7,797,999 B2 * | 9/2010 | Takiguchi .................. | 73/584 |
| 2006/0021437 A1 | 2/2006 | Kaduchak et al. | |
| 2009/0139332 A1 * | 6/2009 | Goddard et al. ............. | 73/570 |

FOREIGN PATENT DOCUMENTS

JP 09-508703 9/1997

OTHER PUBLICATIONS

Bruce C. Towe, PhD, "Use of Piezoelectric Materials as Markers in Ultrasound Imaging," Proceedings of the First Joint BMES/EMBS Conference Serving Humanity, Advancing Technology, p. 1063, ( Oct. 13-16, 1999).

European Search Report dated Dec. 10, 2009 issued by the European Patent Office in corresponding European Patent Application No. 07 25 4180.

* cited by examiner

*Primary Examiner* — John Fitzgerald
(74) *Attorney, Agent, or Firm* — Finnegan, Henderson, Farabow, Garrett & Dunner, L.L.P.

(57) ABSTRACT

A marker detection apparatus detects a marker attached to a target sample from samples flowing in a sample flow, including: an electric field formation section that forms a quasi-electrostatic field in a path of the sample flow; and a detection section that detects, when the target sample labeled by the marker that is a particle made from a piezoelectric or electrostrictive substance of a unique vibration frequency gets into the quasi-electrostatic field, the vibration of the particle.

9 Claims, 15 Drawing Sheets

| TARGET SAMPLES | MARKER ATTACHED TO TARGET SAMPLES | | | CHARGE VOLTAGE |
|---|---|---|---|---|
| $C_1$ | $f_1$ | | | $VG_1$ |
| $C_2$ | | $f_2$ | | $VG_2$ |
| $C_3$ | $f_1$ | | $f_3$ | $VG_3$ |
| . | | | | . |
| $C_N$ | $f_1$ | $f_2$ | $f_4$ | $VG_N$ |

MARKER DETECTION APPARATUS AND MARKER DETECTION METHOD

CROSS REFERENCES TO RELATED APPLICATIONS

The present invention contains subject matter related to Japanese Patent Application JP2006-287898 filed in the Japanese Patent Office on Oct. 23, 2006, the entire contents of which being incorporated herein by reference.

BACKGROUND OF THE INVENTION

1. Field of the Invention

The present invention relates to a marker detection apparatus and marker detection method, and is preferably applied to a flow cytometry technique, for example.

2. Description of the Related Art

There are methods to retrieve a target living cell from various cells, and one of them is flow cytometry. Flow cytometry uses a flow or stream: the target samples, labeled by fluorescent substances or a marker under a certain condition, are put into the flow one by one. In addition, a laser beam is directed onto the droplets of the flow at a right angle.

There is a flow cytometer that has an optical component to sort the scattered or fluorescent light (which was excited as a result of emitting the laser beam) by wavelength and then leads it to a corresponding detector to detect whether the marker exists (see Jpn. Pat. Laid-open Publication H9-508703). In this manner, the flow cytometer separates the target sample or a target cell labeled by a specific marker from other substances such as cells attached to other markers or cells with no markers.

SUMMARY OF THE INVENTION

However, the above flow cytometer has limitation in detecting the small markers, which is determined by the wavelength of the laser beam. This means that the flow cytometer may not be able to detect the markers smaller than around 340 nm to 633 nm. Accordingly, the flow cytometer may need some adjustment or calibration of the optical components to precisely detect those small markers.

The present invention has been made in view of the above points and is intended to provide a marker detection apparatus and marker detection method that can accurately detect a marker.

In one aspect of the present invention, a marker detection apparatus detects a marker attached to a target sample from samples flowing in a sample flow, including: an electric field formation section that forms a quasi-electrostatic field in a path of the sample flow; and a detection section that detects, when the target sample labeled by the marker that is a particle made from a piezoelectric or electrostrictive substance of a unique vibration frequency gets into the quasi-electrostatic field, the vibration of the particle.

Accordingly, the apparatus can detect the vibration of the particle, which is caused by the inverse piezoelectric effect, by using the quasi-electrostatic field generated in a limited space without depending on the wavelength. Thus, the apparatus can detect the smaller markers than the typical laser-type apparatus can.

In addition, since the apparatus generates the quasi-electrostatic field in an area including the sample flow, the apparatus can detect the markers behind the direction of the emitted laser beam, while the typical laser-type apparatus, which is designed to emit the straight laser beam in a direction perpendicular to the layer flow, may not be able to detect.

In another aspect of the present invention, a marker detection apparatus detects a marker attached to a target sample from samples flowing in a sample flow, including: an elastic wave applying section that applies an elastic wave to a path of the sample flow; and a detection section that detects, when the target sample labeled by the marker that is a particle made from a piezoelectric or electrostrictive substance of a unique vibration frequency flows in the sample flow, a quasi-electrostatic field that is generated on the particle due to the piezoelectric or electrostrictive effect of the particle as a result of applying the elastic wave.

Accordingly, the apparatus can detect the vibration of the particle, which is caused by the piezoelectric effect, by using the quasi-electrostatic field generated in a limited space without depending on the wavelength. Thus, the apparatus can detect the smaller markers than the typical laser-type apparatus can.

In addition, since the quasi-electrostatic field generated on the particle as a result of applying the elastic wave goes around the target sample, the apparatus can detect the markers behind the direction of the emitted laser beam, while the typical laser-type apparatus, which is designed to emit the straight laser beam in a direction perpendicular to the layer flow, may not be able to detect.

According to the present invention, the marker detection apparatus detects the vibration of the particle (piezoelectric or electrostrictive substance), which is caused by the inverse piezoelectric effect or the piezoelectric effect, by using the quasi-electrostatic field. Thus, the marker detection apparatus and marker detection method according to an embodiment of the present invention can accurately detect a marker.

The nature, principle and utility of the invention will become more apparent from the following detailed description when read in conjunction with the accompanying drawings in which like parts are designated by like reference numerals or characters.

DETAILED DESCRIPTION OF PREFERRED EMBODIMENTS

Figure 1:
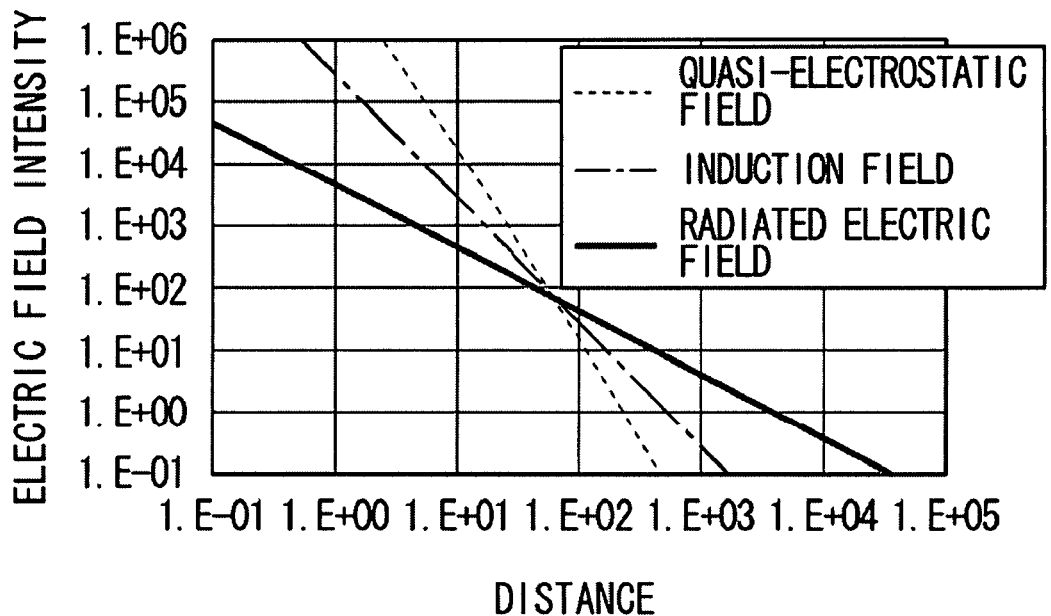
FIG. 1 is a schematic diagram illustrating how the intensity of electric fields change with distance (1 MHz)

An embodiment of the present invention will be described in detail with reference to the accompanying drawings.

(1) Electric Field

In this embodiment, a quasi-electrostatic field is used to detect a target sample labeled or marked by a marker. Various aspects of the electric field will be described, followed by description of the present embodiment for identifying the samples.

(1-1) Classification of the Electric Field

According to the Maxwell equations, an electric field intensity E at a position P is represented as follows:

$$E_r = \frac{Ql\cos\theta}{2\pi\varepsilon r^3}(1+jkr)\exp(-jkr) \quad (1)$$

$$E_\theta = \frac{Ql\sin\theta}{4\pi\varepsilon r^3}(1+jkr+(jkr)^2)\exp(-jkr)$$

wherein "r" is a distance from an infinitesimal dipole or an electric field source to the position P. In this manner, the electric field intensity E is represented as a polar coordinate (r, θ, δ). By the way, in the above equation (1), "Q" means an electric charge C, "l" represents a distance between the electric charges (according to the definition of the infinitesimal dipole, "l" is smaller than "r"), "π" is the circle ratio, "ε" is a dielectric constant for a space including the infinitesimal dipole, "j" is an imaginary unit and "k" represents the number of waves.

Developing the equation (1) gives:

$$E_r = \frac{Ql\cos\theta}{2\pi\varepsilon r^3} \cdot \exp(-jkr) + \frac{Ql\cos\theta}{2\pi\varepsilon r^3} \cdot jkr \cdot \exp(-jkr) \quad (2)$$

$$E_\theta = \frac{Ql\sin\theta}{4\pi\varepsilon r^3} \cdot \exp(-jkr) +$$

$$\frac{Ql\sin\theta}{4\pi\varepsilon r^3} \cdot jkr \cdot \exp(-jkr) + \frac{Ql\sin\theta}{4\pi\varepsilon r^3} \cdot (jkr)^2 \cdot \exp(-jkr)$$

It is evident from the equation (2) that the electric fields $E_r$ and $E_\theta$ are generated as the combination of: a radiated electric field (the third element of the equation of $E_\theta$), which linearly and inversely varies according to the distance from the electric field source; an induction field (the second element of the equations of $E_r$ and $E_\theta$), which is inversely proportional to the square of the distance from the electric field source; and a quasi-electrostatic field (the first element of the equations of $E_r$ and $E_\theta$), which is inversely proportional to the cube of the distance from the electric field source.

In that manner, according to the distance, the electric field is classified into the radiated electric field, the induction field and the quasi-electrostatic field.

(1-2) Correlation Between Electric Field and Resolution

The electric field intensity changes according to the distance from the electric field source, as for the radiated electric field, the induction field and the quasi-electrostatic field. As for the equation (2), differentiating the third element of $E_\theta$ (i.e. the radiated electric field) with respect r gives:

$$\frac{dE_{\theta 1}}{dr} = -\frac{1}{r^2}T \quad (3)$$

As for the equation (2), differentiating the second element of $E_\theta$ (i.e. the induction field) with respect r gives:

$$\frac{dE_{\theta 2}}{dr} = -2\frac{1}{r^3}T \quad (4)$$

As for the equation (2), differentiating the first element of $E_\theta$ (i.e. the quasi-electrostatic field) with respect r gives:

$$\frac{dE_{\theta 3}}{dr} = -3\frac{1}{r^4}T \quad (5)$$

By the way, part of the above equations (3) to (5) is replaced by T:

$$T = \frac{Ql\cos\theta}{2\pi\varepsilon r^3} \cdot \exp(-jkr) \quad (6)$$

It is evident from the above equations (3) to (5) that the quasi-electrostatic field has the highest ratio of change of the electric field intensity.

That means that the quasi-electrostatic field has higher resolution to the distance than the radiated electric field and the induction field.

In that manner, the electric field source produces the radiated electric field, the induction field and the quasi-electrostatic field. And if the intensity of the target quasi-electrostatic field is stronger than that of the radiated electric field and the induction field, it is possible to assume that the radiated electric field and the induction field are not there. Thus, the quasi-electrostatic field can be detected.

(1-3) Correlation Between Electric Field and Frequency

FIG. 1 is a graph illustrating correlation of relative intensities between the radiated electric field, the induction field and the quasi-electrostatic field and the distance. FIG. 1 uses exponents to describe the correlation between the relative intensities of the electric fields (1 MHz) and the distance.

It is evident from FIG. 1 that there is a distance (also referred to as an "intensity boundary") where the relative intensities of the radiated electric field, the induction field and the quasi-electrostatic field become equal to each other. In this case, the radiated electric field is predominant (over the induction field and the quasi-electrostatic field) in an area beyond the intensity boundary while the quasi-electrostatic field is predominant (over the induction field and the radiated electric field) inside the intensity boundary.

The electric fields ($E_{\theta 1}$, $E_{\theta 2}$ and $E_{\theta 3}$) are represented as follows:

$$E_{\theta 1} = \frac{Ql\sin\theta}{4\pi\varepsilon r^3} \cdot \exp(-jkr) \quad (7)$$

$$E_{\theta 2} = \frac{Ql\sin\theta}{4\pi\varepsilon r^3} \cdot jkr \cdot \exp(-jkr)$$

$$E_{\theta 3} = \frac{Ql\sin\theta}{4\pi\varepsilon r^3} \cdot (jkr)^2 \cdot \exp(-jkr)$$

Accordingly, at the intensity boundary, those electric fields are equal to each other ($E_{\theta 1}=E_{\theta 2}=E_{\theta 3}$). This means:

$$1 = jkr = (jkr)^2 \quad (8)$$

The above equation (8) can also be represented as follows:

$$r = \frac{1}{k} \quad (9)$$

In addition, "k" indicating the number of waves in the equation (9) is also represented as follows:

$$k = \frac{2\pi f}{c} \quad (10)$$

wherein "c" is velocity of light ($c=3\times10^8$ m/s) and "f" represents frequency.

Accordingly, based on the above equations (9) and (10), the intensity boundary is defined as follows:

$$r = \frac{c}{2\pi f} \quad (11)$$

It is evident from the equation (11) that the frequency is important when the space of the quasi-electrostatic field, whose intensity is stronger than the radiated electric field and the induction field, is widened. By the way, the space of the quasi-electrostatic field, whose intensity is stronger than the radiated electric field and the induction field, is also referred to as a "quasi-electrostatic field dominant space".

That means that the lower the frequency is, the larger the quasi-electrostatic field dominant space will be (This means that the distance to the intensity boundary (FIG. 1) becomes longer as the frequency is getting lower (i.e. the intensity boundary moves in the right direction on the graph)). On the other hand, the higher the frequency is, the narrower the quasi-electrostatic field dominant space will be (This means that the distance to the intensity boundary (FIG. 1) becomes shorter as the frequency is getting higher (i.e. the intensity boundary moves in the left direction on the graph)).

Figure 2:
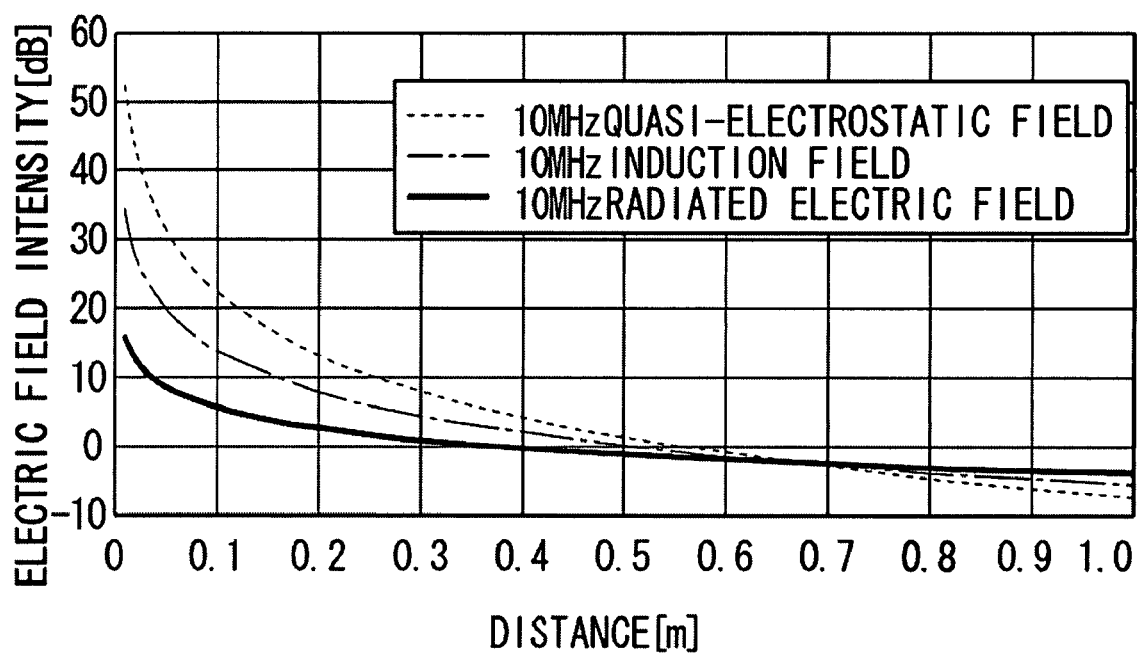
FIG. 2 is a schematic diagram illustrating how the intensity of electric fields change with distance (10 MHz)

According to the equation (11), the boundary of the quasi-electrostatic field dominant space is 0.675 m when the frequency is 10 MHz. FIG. 2 illustrates the intensities and distances regarding the radiated electric field, the induction field and the quasi-electrostatic field when the frequency is 10 MHz.

As shown in FIG. 2, the intensity of the quasi-electrostatic field is 18.2 dB stronger than that of the induction field at 0.01 m away from the electric field source. Accordingly, the effect of the radiated electric field and the induction field can be ignored at this point.

In that manner, when the frequency is set at low level, the quasi-electrostatic field is predominant over the radiated electric field and the induction field around the electric field source and the space of the quasi-electrostatic field becomes larger.

That is, when the frequency is set at low level, the intensity of the target quasi-electrostatic field is stronger than that of the out-of-target radiated electric field and induction field around the electric field source. Therefore, the quasi-electrostatic field is detected to accurately identify samples.

(2) An Embodiment of the Present Invention

Following describes an embodiment of the present invention in detail.

(2-1) Overall Configuration of a Flow Cytometer

Figure 3:
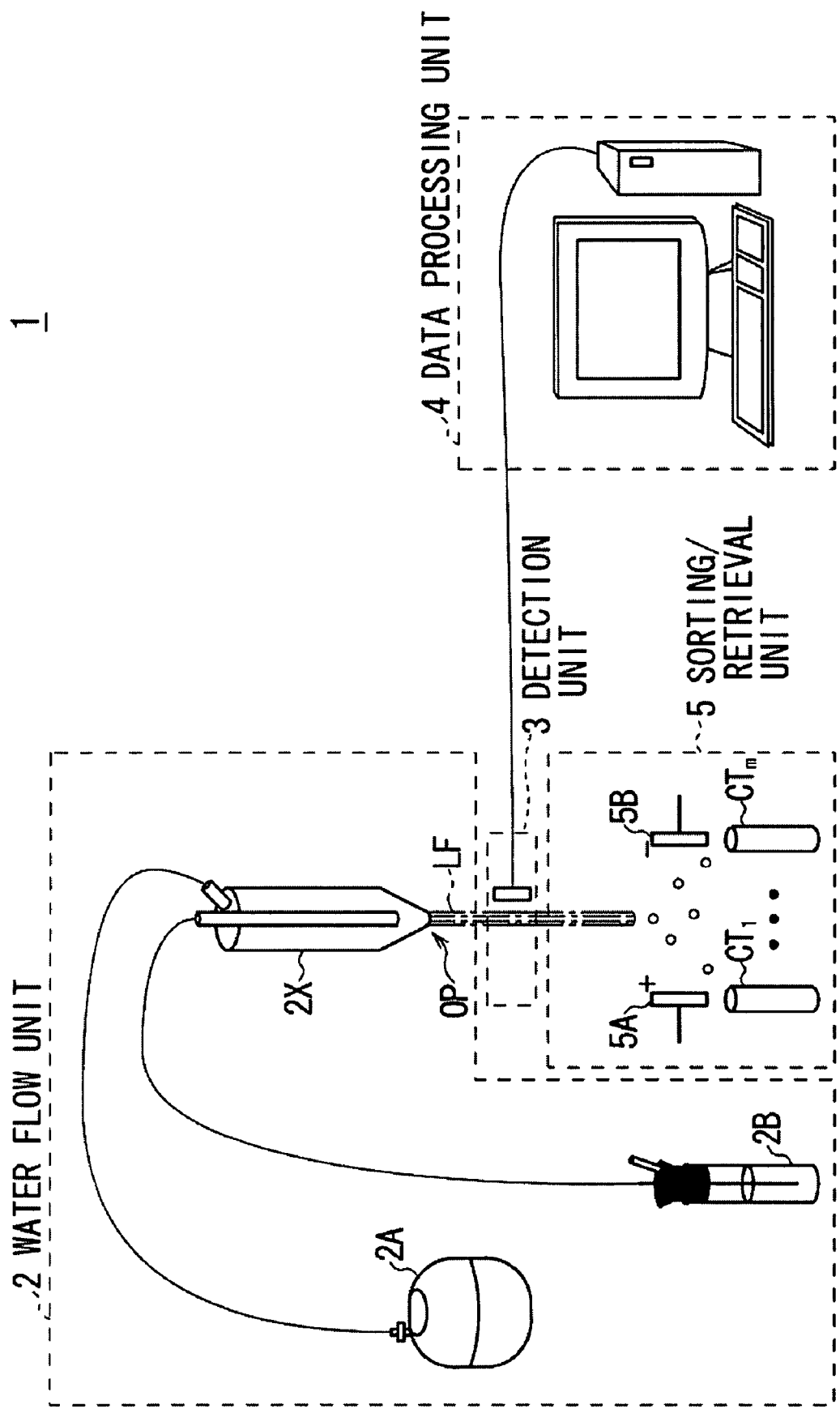
FIG. 3 is a schematic diagram illustrating the overall configuration of a flow cytometer according to an embodiment of the present invention.

FIG. 3 illustrates a flow cytometer according to an embodiment of the present invention. The flow cytometer 1 includes a water flow unit 2, a detection unit 3, a data processing unit 4 and a sorting/retrieval unit 5

The water flow unit 2 includes a sheath flow generation section 2A that gives a predetermined sheath pressure to produce a sheath flow, which is then supplied via a sheath tube to an interflow chamber 2X. The water flow unit 2 also includes a sample flow generation section 2B that gives a predetermined sample pressure to generate a sample flow, which is then supplied via a sample tube to the interflow chamber 2X. As a result, the combined stream or layer flow LF spouts out from an outlet OP of a nozzle of the interflow chamber 2X, the sample flow being in the center of the combined stream while the sheath flow in the rim of the stream.

In line with the principle of Laminar Flow, the water flow unit 2 is designed to control the layer flow FL: The sample flow does not mixed up with the sheath flow covering the sample flow and each sample flows separately in the sample flow.

The equation about the layer flow FL is defined as follows:

$$R = \frac{\rho a U}{\eta} \quad (12)$$

wherein "ρ" is fluid density of the layer flow LF, "a" is an inside diameter of the outlet OP, "U" is fluid velocity and "η" is fluid viscosity.

The layer flow LF is turbulent when R>1000. On the other hand, the layer flow LF is stable when R<1000. Such a state of the layer flow LF with R<1000 is known as laminar flow. Since fluid viscosity largely depends on temperature, the sheath flow generation section 2A appropriately controls temperature for the sheath flow.

The detection unit 3 is placed in the path of the layer flow. By using a quasi-electrostatic field, the detection unit 3 electrically detects a marker (label substance) attached to target samples, each of which separately exists in the sample flow. The detection unit 3 subsequently supplies resulting detection data to the data processing unit 4.

The data processing unit 4 is a computer to identify the type of the target sample from the detection data. After identifying the type, the data processing unit 4 decides how much charge voltage it will apply to the target sample.

The sorting/retrieval unit 5 applies the charge voltage, determined by the data processing unit 4, to the sample flow when the layer flow LF breaks into droplets (break off point). As a result, the charged droplet including the target sample is broken off from the layer flow LF by a positive deflection plate 5A with a predetermined voltage and a negative deflection plate 5B with a predetermined voltage, flowing into one of collection tubes CT1 to CTm (m=2, 3, . . . ).

In that manner, the flow cytometer 1 identifies and sorts out the target sample.

(2-2) Marker

The following describes the marker attached to the target samples. The marker is used to identify the sample.

The marker used in this embodiment is a piezoelectric substance of a certain vibration frequency, including a piezoelectric crystal, a piezoelectric ceramics, a piezoelectric thin film, a piezoelectric polymer substance and a ferrodielectric substance (also known as relaxor).

The piezoelectric substance can be: crystal ($SiO_2$), lithium niobate ($LiNbO_3$), barium titanate ($BaTiO_3$), lead titanate ($PbTiO_3$), lead zirconate titanate (PZN), lead metaniobate ($PbNb_2O_6$), polyvinylidene fluoride (PVDF) and zinc oxide (ZnO).

The piezoelectric substance also can be: lithium tantalite ($LiTaO_3$), potassium niobate ($K_4NbO_3$), lithium tetraborate ($Li_2B_4O_7$), langasite ($La_3Ga_5SiO_{14}$), aluminum nitride (AlN) and tourmaline.

The method of attaching the marker (i.e. piezoelectric substance) to a target sample is: attaching the piezoelectric substance to a probe that is specific to a distinctive part of the target sample and then attaching the probe with the piezoelectric substance to the distinctive part of the target sample.

The probe can be an antibody. This kind of probe is used to detect a certain cell because an antibody is attached to the corresponding antigen by the primary antibody method, the secondary antibody method or affinity of avidin/biotin.

The probe may also include Annexin V, and MHC class I—peptide tetramer and the like. They are a high molecular weight protein of the immunoglobulin superfamily, used for detecting apoptotic cells or antigen-specific CD8$^+$T cells.

In addition, there are probes, such as DNA oligomer or RNA oligomer, which utilizes characteristic of complementary binding of DNA and RNA. Those probes are used to detect the sequences of DNA or RNA because they attach to a specific sequence by hybridization.

On the other hand, there are methods to attach the piezoelectric substance to the probes. One of the methods is directly attaching the piezoelectric substance to the probes. The other is attaching the piezoelectric substance to the probes through organic polymeric materials such as dextran, albumin, starch, polyacrylamide and polyethylene glycol (refer to: Inada Yuji, protein hybridization Vol. 3, Kyoritsu Shuppan Co., Ltd. 1990).

Figure 4:
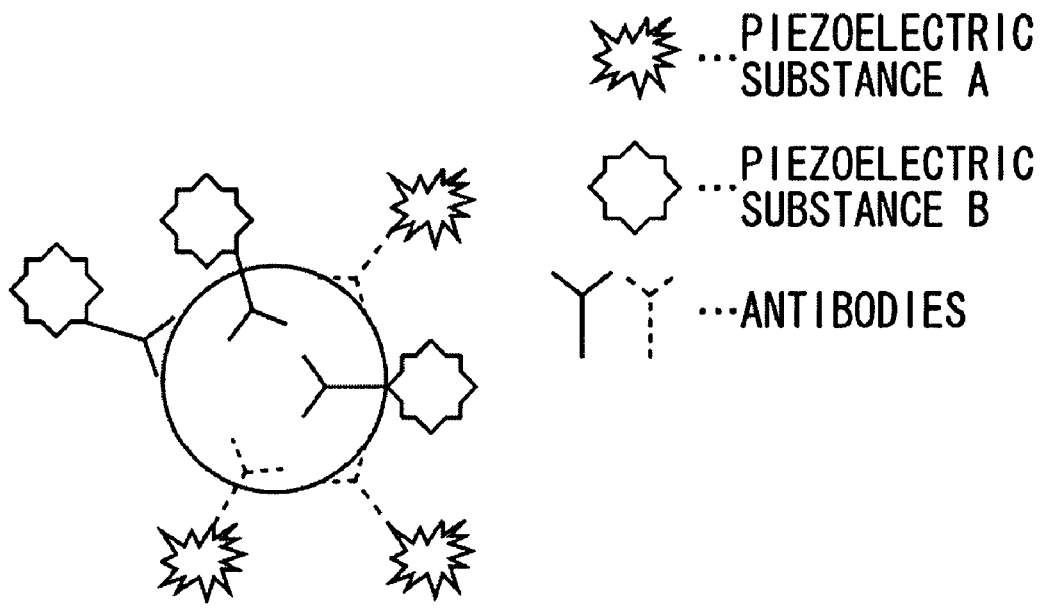
FIG. 4 is a schematic diagram illustrating piezoelectric substances attached to a target cell.

By the way, if two or more markers are used for detecting a target cell, each of them may be a piezoelectric substance of a different vibration frequency to be attached to the target cell. For example, when there is a target sample with two specific antigens as shown in FIG. 4, the piezoelectric substances (A and B), each of which has a different vibration frequency, are attached to the antigens through corresponding antibodies or probes. In this manner, one or more unique piezoelectric substances are attached to the target sample.

(2-3) Configuration of the Detection Unit

Figure 5:
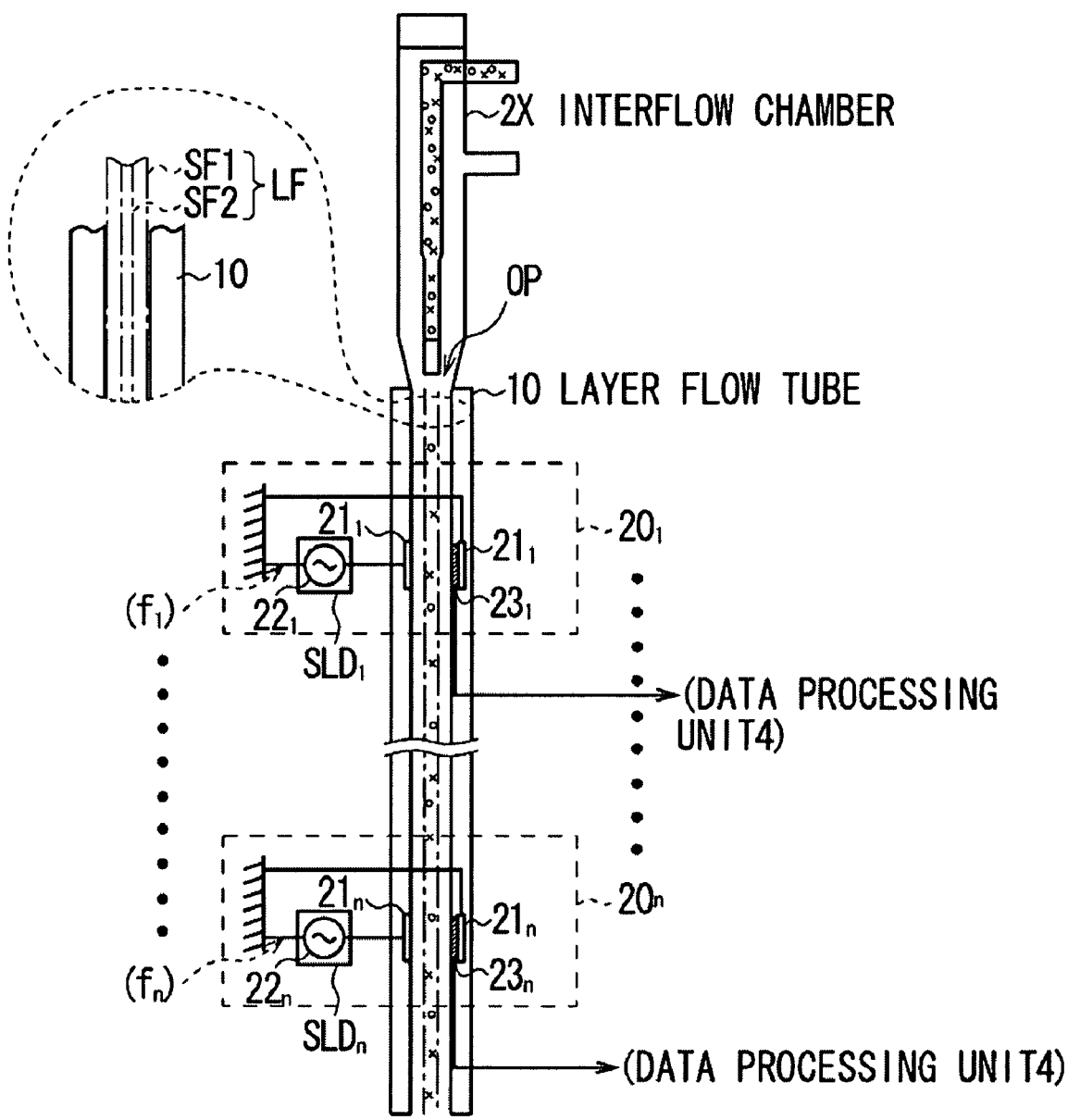
FIG. 5 is a schematic diagram illustrating the configuration of a detection unit.

FIG. 5 illustrates the configuration of the detection unit 3. The detection unit 3 includes a layer flow tube 10 and a plurality of marker detection sections $20_1$ to $20_n$.

The layer flow tube 10 is connected to the interflow chamber 2X of the water flow unit 2. The layer flow tube 10 is placed such that the inner wall of the layer flow tube 10 surrounds or covers the outer layer of the layer flow LF emerging from the outlet OP of the nozzle of the interflow chamber 2X.

The marker detection sections $20_1$ to $20_n$ (n=2, 3, . . . ) utilizes the inverse piezoelectric effect to detect the piezoelectric substances of unique vibration frequencies. The marker detection sections $20_1$ to $20_n$ includes parallel plane electrodes $21_1$ to $21_n$, sine wave signal output sections $22_1$ to $22_n$ and elastic wave detection sections $23_1$ to $23_n$.

The parallel plane electrodes $21_1$ to $21_n$, placed between the outer and inner walls of the layer flow tube 10, are provided along the layer flow at certain intervals so that a pair of the parallel plane electrodes faces each other. Accordingly, when the nozzle's outlet OP spouts out the layer flow FL, the samples in the sample flow SF2 flows through between the parallel plane electrodes $21_1$ to $21_n$.

The sine wave signal output sections $22_1$ to $22_n$ are covered by shields $SLD_1$ to $SLD_n$ and connected to the corresponding parallel plane electrodes $21_1$ to $21_n$. FIG. 5 shows the connection lines that look like passing through the layer flow tube 10. However, in fact, those lines are passing through a predetermined path.

The sine wave signal output sections $22_1$ to $22_n$ outputs the sine-wave alternating voltage whose frequencies are the same as the vibration frequencies ($f_1$ to $f_n$) of the piezoelectric substance that is selected as a target out of the piezoelectric substances of different unique vibration frequencies. Those frequencies ($f_1$ to $f_n$) are determined such that, in an area from a reference position to a target position (which is also referred to as a "detection target area"), the intensity of the quasi-electrostatic field (which is in inverse proportion to the cube of the distance from the reference position) is stronger than the intensity of the induction field (which is in inverse proportion to the square of the distance from the reference position).

The detection target area is determined based on a distance from the parallel plane electrodes $21_1$ to $21_n$ to the sample flow SF2 and a distance between the parallel plane electrodes facing each other. For example, when the detection target area extends 1 cm from the parallel plane electrodes, "r" of the above equation (11) is 0.01 m and therefore the frequency is 4.7 GHz.

Figure 6:
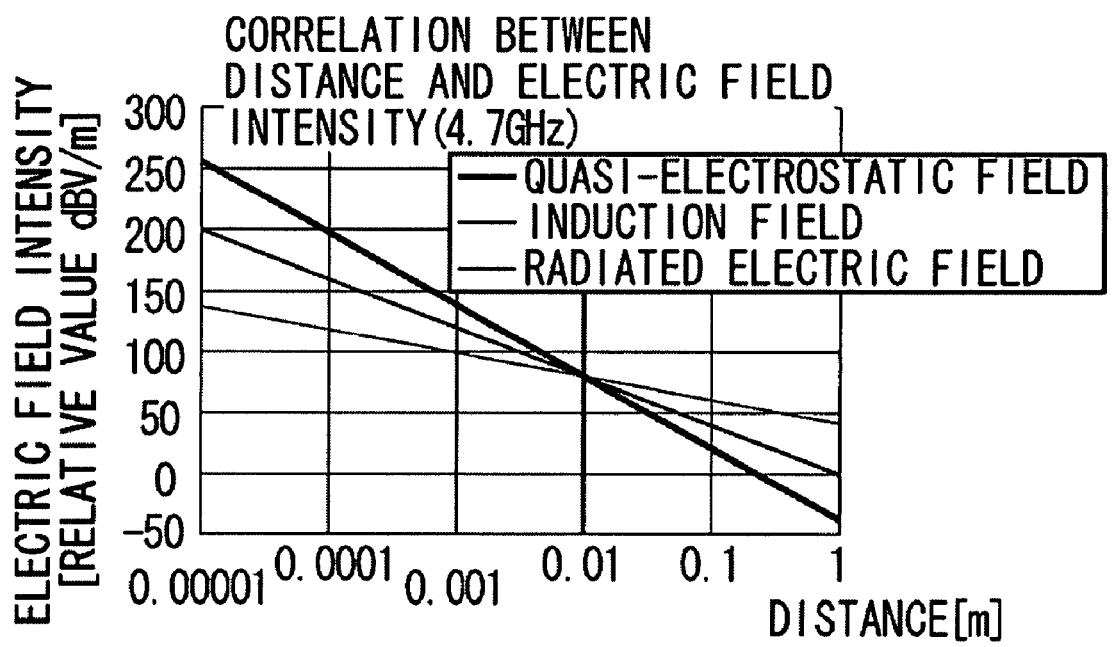
FIG. 6 is a schematic diagram illustrating the intensity of electric field when an intensity boundary is 0.01 m.

Accordingly, as shown in FIG. 6, in a case in which the intensity boundary of the radiated electric field, induction field and quasi-electrostatic field is 0.01 m, the intensity of the generated quasi-electrostatic field is larger than that of the radiated electric field and the induction field if the frequency is lower than 4.7 GHz.

Figure 7:
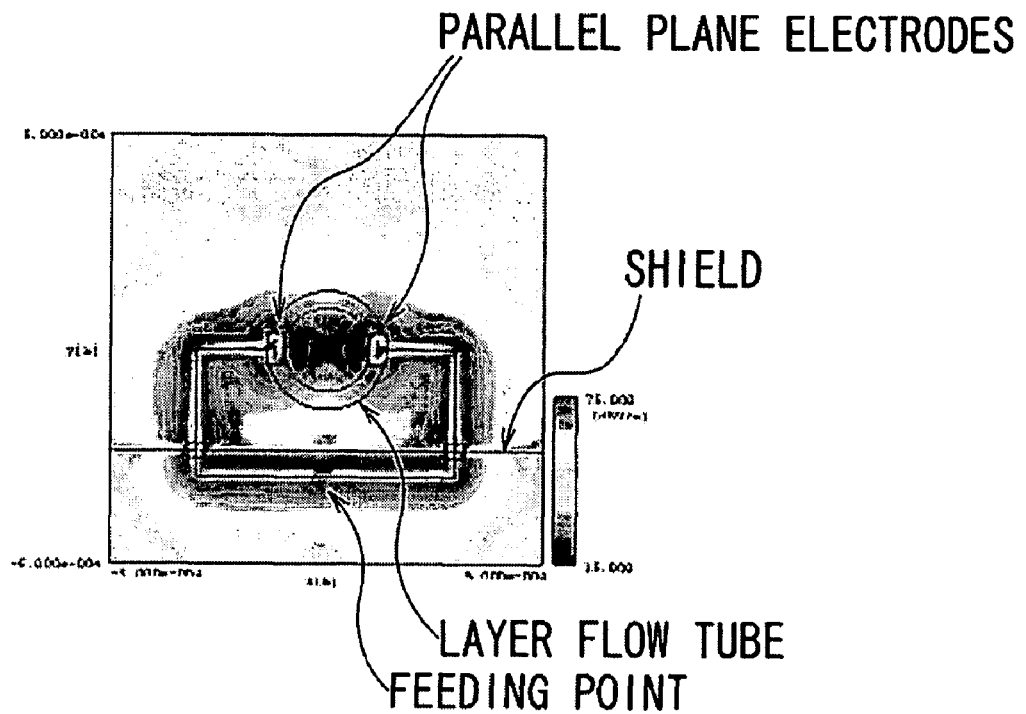
FIG. 7 is a schematic diagram illustrating the result of simulation regarding an electric field intensity distribution pattern (1)
Figure 8:
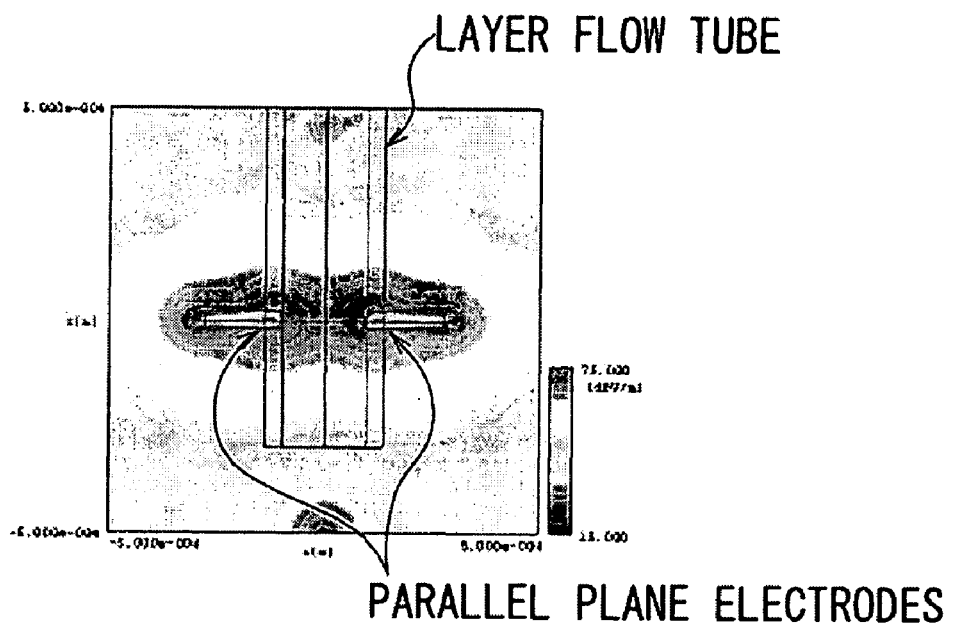
FIG. 8 is a schematic diagram illustrating the result of simulation regarding an electric field intensity distribution pattern (2)

FIGS. 7 and 8 illustrate the quasi-electrostatic field generated from the parallel plane electrodes. FIG. 7 is a cross sectional view of the layer flow tube in the horizontal direction (or a direction perpendicular to the layer flow) while FIG. 8 is a cross sectional view of the layer flow tube in the vertical direction (or a direction parallel to the layer flow).

In this case of FIGS. 7 and 8, the simulation runs under the condition that: the frequency or a feeding wave is 10 MHz; the amplitude of the feeding wave is 1 V; the outer diameter of the layer flow tube is 280 μm; the inner diameter of the layer flow tube is 200 μm; the relative permittivity of the layer flow tube is 2; the electric conductivity of the layer flow tube is 0 S/m; the relative permittivity of the normal saline solution that passes through the layer flow tube is 80; and the electric conductivity of the solution is 2 S/m. The attached reference drawing 1 uses several colors to illustrate the distribution pattern of the electric field intensity (also shown in FIG. 7) while the attached reference drawing 2 uses several colors to illustrate the distribution pattern of the electric field intensity (also shown in FIG. 8).

By the way, that simulation uses a general electromagnetic wave analyzing software called "Mathematical Assist Design Laboratory Corporation (EEM-FDM)". This software calculates impedance between electric fields, magnetic fields and feeding electrodes by digitizing the specified frequency based on the difference method of the Maxwell equations.

As shown in FIGS. 7 and 8, the intensity of the quasi-electrostatic field is strong around the parallel plane electrodes. The intensity of the quasi-electrostatic field becomes weaker with distance from the parallel plane electrodes. The quasi-electrostatic field does not expand so much through the normal saline solution. The quasi-electrostatic field is generated only around the parallel plane electrodes.

In that manner, the sine wave signal output sections $22_1$ to $22_n$ supplies to the corresponding parallel plane electrodes a plurality of levels of sine-wave alternating voltage, whose frequencies are the same as the corresponding piezoelectric substances' vibration frequencies and are also lower than a certain frequency at which the intensities of the radiated electric field, the induction field and the quasi-electrostatic field become equal to one another in the detection target area. As a result, the quasi-electrostatic field dominant space (or quasi-electrostatic field) is generated around the parallel plane electrodes.

For example, after the quasi-electrostatic field dominant spaces (or quasi-electrostatic fields) are generated around the parallel plane electrodes $21_1$ to $21_n$, the target sample labeled by two piezoelectric substances of different vibration frequencies may flow in the sample flow SF as shown in FIG. 4. In this case, when the target sample passes through the quasi-electrostatic field whose frequency is the same as the vibration frequency of the piezoelectric substance attached to the target sample, the piezoelectric substance begins to vibrate in its unique vibration frequency (i.e. the inverse piezoelectric effect). Therefore, the corresponding elastic wave detection section 23 detects its vibration distortion as elastic wave.

By the way, the elastic waves do not interfere with the charge voltage, which is applied to the sample flow by the sorting/retrieval unit 5, because the frequency of the elastic waves is different from that of the charge voltage.

Figure 9:
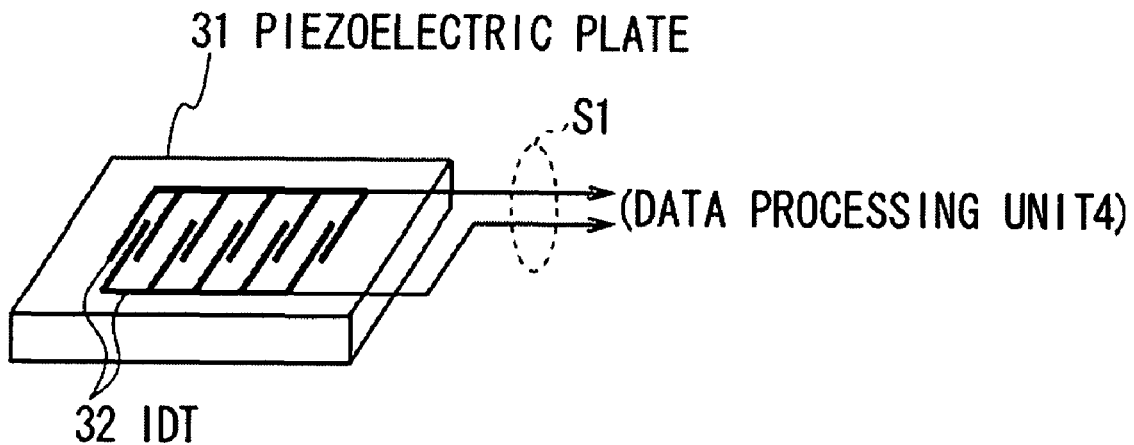
FIG. 9 is a schematic diagram illustrating the configuration of an elastic wave detection section.

On the other hand, the elastic wave detection sections $23_1$ to $23_n$ are placed between one side of the parallel plane electrodes 21 and the inner wall of the layer flow tube 10 (FIG. 5). As shown in FIG. 9, each of the elastic wave detection sections $23_1$ to $23_n$ includes a piezoelectric plate 31 on which an Inter Digital Transducer (IDT) 32 is placed. The piezoelectric plate 31 will be in sympathetic vibration with the elastic waves from the target sample to generate a surface wave (i.e. the piezoelectric effect).

The IDT 32 includes two comb-shaped conductors facing each other as if being interlocked, serving as a filter to extract a certain signal component. The signal component extracted by the IDT 32 varies due to the material of the piezoelectric plate and the interval of the teeth of the comb-like conductors. This can be represented as follows:

$$v = 2d \times f \quad (13)$$

wherein "v" is a propagation speed of the surface wave on the piezoelectric plate of the IDT 32, "2d" represents the interval of the teeth of the comb-like conductors and "f" represents a center frequency of the IDT.

In this embodiment, the IDT 32 of the elastic wave detection sections uses a certain material for the piezoelectric plate with a certain interval regarding the teeth of the comb-like conductors such that they are suitable for the frequencies ($f_1$ to $f_n$) of the sine wave alternating voltage from the corresponding sine wave signal output sections $22_1$ to $22_n$ (FIG. 5). Accordingly, the IDT 32 of the elastic wave detection sections $23_1$ to $23_n$ retrieves a wave of the same frequency as the corresponding piezoelectric substance from the surface waves generated around the piezoelectric plate 31 and then supplies a resulting detection signal S1 to the data processing unit 4 (FIG. 3).

In that manner, the parallel plane electrodes $21_1$ to $21_n$ (which are spaced, along the layer flow, a certain distance from each other) of the detection unit 3 (FIG. 5) generate the quasi-electrostatic field dominant spaces of different frequencies ($f_1$ to $f_n$). When the piezoelectric substance attached to the target sample passes through between the parallel plane electrodes $21_1$ to $21_n$, the piezoelectric substance vibrates in the quasi-electrostatic field whose frequency is the same as that of the piezoelectric substance. The elastic wave detection sections $23_1$ to $23_n$ therefore generate the detection signal S1 representing the fact that the piezoelectric substance of a specific frequency has been detected, and then supplies the detection signal S1 to the data processing unit 4 (FIG. 3).

(2-4) Configuration of the Data Processing Unit

Figure 10:
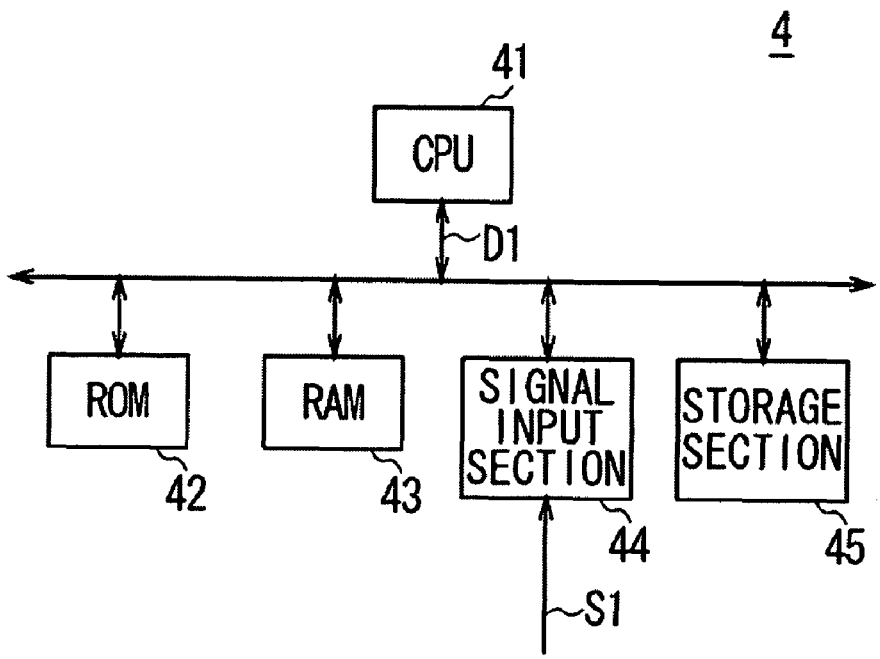
FIG. 10 is a block diagram illustrating the configuration of a data processing unit.

As shown in FIG. 10, the data processing unit 4 includes a Central Processing Unit (CPU) 41 connected to a Read Only Memory (ROM) 42, which stores various programs, a Random Access Memory (RAM) 43, which serves as a work memory for the CPU, a signal input section 44 and a storage section 45.

The signal input section 44 amplifies the detection signal S1, supplied from the IDT 32 (FIG. 9) of the elastic wave detection sections $23_1$ to $23_n$, and then performs an Analog-to-Digital (A/D) conversion process. The signal input section 44 subsequently supplies resultant detection data D1 to the CPU 41.

Figures 11, 12:
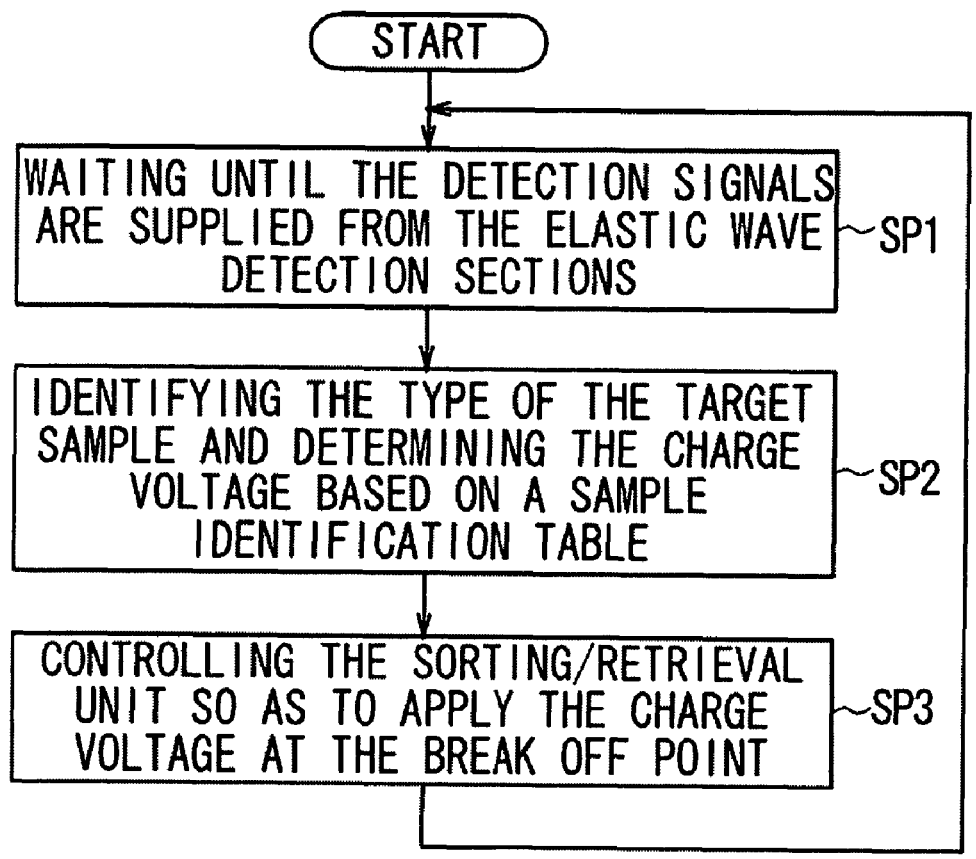
FIG. 11 is a schematic diagram illustrating a sample identification table.
FIG. 12 is a flowchart illustrating the procedure of an analyzing/sorting/retrieval process.

As shown in FIG. 11, the storage section 45 stores a database (also referred to as a "sample identification table") in which the types of the target samples, the condition of the markers (or piezoelectric substances) for the target samples and the values of the charge voltages applied to the target samples are associated with one another.

The CPU 41 executes a program stored in the ROM 42 and then identifies the type of the target sample in the sheath flow, based on the sample identification table and the detection data D1 from the signal input section 44. In addition, the CPU 41 determines how much charge voltage it will apply to the target sample.

FIG. 12 is a flowchart illustrating the process of the CPU 41. When receiving a process start command, the CPU 41 starts running the water flow unit 2, the detection unit 3 and the sorting/retrieval unit 5, and then proceeds to step SP1. At step SP1, the CPU 41 waits until it receives the detection signal S1 from the elastic wave detection sections $23_1$ to $23_n$.

After receiving the detection signal S1 from the elastic wave detection sections $23_1$ to $23_n$, the CPU 41 proceeds to step SP2. At step SP2, the CPU 41 identifies the type of the target sample that has passed through the elastic wave detection sections $23_1$ to $23_n$, based on the detection signal S1 and the sample identification table (FIG. 11) stored in the storage section 45. In addition, the CPU 41 determines how much charge voltage it will apply to the target sample.

Subsequently, the CPU 41 at step SP3 notifies the sorting/retrieval unit 5 of the charge voltage level determined at step SP2 and then returns to step SP1. The sorting/retrieval unit 5 will apply that level of the charge voltage to the sample flow when the droplets break off the flow (break off point). As a result, the charged droplet including the target sample is broken off from the flow by the deflection plate 5A or 5B, flowing into one of collection tubes $CT_1$ to $CT_m$.

In that manner, the data processing unit 4 analyzes the target samples based on the detection result of the detection unit 3. In addition, the data processing unit 4 controls the sorting/retrieval unit 5 such that each collection tube CT collects a corresponding target sample.

(3) Operation and Effect

The flow cytometer 1 includes the parallel plane electrodes 21 (adjacent to the layer flow LF) to generate the quasi-electrostatic field along the path of the layer flow LF. The elastic wave detection sections 23 detect vibration of the piezoelectric substance (or the elastic wave) when the piezoelectric substance attached to the target sample gets into the quasi-electrostatic field.

In this manner, the flow cytometer 1 utilizes the quasi-electrostatic field, which is generated within a limited space area without depending on the wavelength. This enables the flow cytometer 1 to detect the vibration (elastic wave) arising from the inverse piezoelectric effect of the piezoelectric substance. Accordingly, the flow cytometer 1 can detect the smaller markers than a typical laser type apparatus can detect (the typical laser type apparatus may not be able to detect the markers smaller than the wavelength of its laser beam).

In addition, the quasi-electrostatic field is generated in a space area including the cut plane of the sample flow SF2. This enables the flow cytometer 1 to detect the markers behind the direction of the emitted laser beam, while the typical laser type apparatus, which uses the straight laser beam traveling in a direction perpendicular to the layer flow LF, may not be able to detect them.

When the flow cytometer 1 generates the quasi-electrostatic field from the parallel plane electrodes 21 in an area including the parallel plane electrodes 21, the sample flow SF2 and the elastic wave detection sections 23, the sine wave signal output sections 22 outputs a signal of a certain frequency such that the intensity of the quasi-electrostatic field becomes stronger than that of the induction field.

Accordingly, in the flow cytometer 1, the quasi-electrostatic field generated from the parallel plane electrodes 21 is predominant over the radiated electric field and induction field generated from the parallel plane electrodes 21 around the elastic wave detection sections 23. Accordingly, the elastic wave detection sections 23 can detect the piezoelectric substance attached to the target sample in the sample flow SF2.

The flow cytometer 1 includes a plurality of parallel plane electrodes 21 and elastic wave detection sections 23 to detect a plurality of vibration particles (piezoelectric substances or electrostrictive substances) of different vibration frequencies: One detection unit is a pair of a parallel plane electrode 21 and an elastic wave detection section 23. Those detection units are spaced a predetermined distance away from each other so as to prevent the quasi-electrostatic fields from the parallel plane electrodes 21 from affecting each other.

Accordingly, each detection unit detects a piezoelectric substance of a certain vibration frequency from the layer flow. This enables the flow cytometer 1 to precisely detect the piezoelectric substances of different vibration frequencies even if there are various piezoelectric substances attached to the target sample.

Moreover, the flow cytometer 1 according to the present embodiment can be downsized, compared to a typical laser-type flow cytometer that includes complex optical components for sorting out various types of scattered beams into corresponding detectors in order to detect the target samples labeled by various fluorescent markers.

Furthermore, the flow cytometer 1 has the layer flow tube 10 that carries the layer flow LF as if it surrounds the surface of the layer flow LF. Between the inner and outer walls of the layer flow tube 10 are placed the parallel plane electrodes 21 and the elastic wave detection sections 23 to make the parallel plane electrodes 21 and the elastic wave detection sections 23 close to the sample flow SF2. This allows the flow cytometer 1 to produce the small quasi-electrostatic fields. That also eliminates the effect of noise for precise detection.

According to the above configuration, by using the quasi-electrostatic fields, the flow cytometer 1 detects the vibration caused by the inverse piezoelectric effect regarding the piezoelectric or electrostrictive substances. Thus, the flow cytometer 1 can precisely detect the target samples.

(4) Other Embodiment

In the above-noted embodiment, the piezoelectric substances are used as the markers. However, the present invention is not limited to this. The markers may include electrostrictive materials. The electrostrictive materials represents: When an electric field is applied to the crystal, the resulting strain will be proportional to the square of the polarization. The electrostrictive materials may be useful because there is no need for polarizing process for the electrostrictive materials (while the piezoelectric substance may need the polarizing process) and they have a symmetrical appearance.

Moreover, in the above-noted embodiment, as a signal output means for the electric field source, the sine wave signal output sections $22_1$ to $22_n$ are connected to the corresponding parallel plane electrodes $21_1$ to $21_n$. However, the present invention is not limited to this. Alternatively, a sine wave signal output section may be connected to the parallel plane electrodes $21_1$ to $21_n$ through a constant voltage variable frequency control section that adjusts the sine wave alternating voltage from the sine wave signal output section to supply a plurality of frequencies of alternating voltage to the parallel plane electrodes.

Furthermore, in the above-noted embodiment, the parallel plane electrodes $21_1$ to $21_n$ between the outer and inner walls of the layer flow tube 10 are spaced, along the layer flow, a certain distance from each other. However, the present invention is not limited to this. Alternatively, the parallel plane electrodes $21_1$ to $21_n$ may be placed outside the layer flow tube 10. Otherwise, the flow cytometer 1 may not have the layer flow tube 10.

Furthermore, in the above-noted embodiment, the flow cytometer 1 includes, as an electric field formation means, the parallel plane electrodes $21_1$ to $21_n$ (which are placed between the outer and inner walls of the layer flow tube 10 and are spaced, along the layer flow, a certain distance from each other) and the sine wave signal output sections $22_1$ to $22_n$ (which apply the sine wave alternating voltage whose frequency is set such that the intensity of the quasi-electrostatic field becomes stronger in the detection target area). The flow cytometer 1 also includes, as a detection means, the detection unit 3 including the elastic wave detection sections $23_1$ to $23_n$. However, the present invention is not limited to this. The flow cytometer may be configured in a different way.

Figure 13:
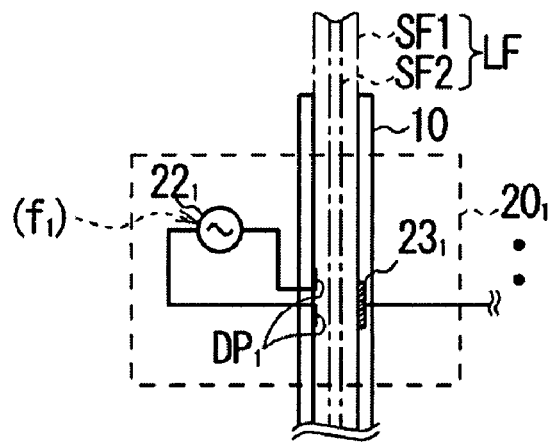
FIG. 13 is a schematic diagram illustrating a detection unit (1) according to another embodiment of the present invention.

For example, the flow cytometer may have a detection unit as shown in FIG. 13 (the parts of FIG. 13 are represented by the same reference numerals and symbols as the corresponding parts of FIG. 5). For ease of explanation, FIG. 13 only illustrates the marker detection sections $20_1$, while FIG. 5 illustrates the marker detection sections $20_1$ to $20_n$.

Instead of the parallel plane electrodes $21_1$, the detection unit (FIG. 13) includes an infinitesimal dipole $DP_1$ as the electric field source, which faces the elastic wave detection section $23_1$ on the outer wall of the layer flow tube. This also presents the same effect as the above-noted embodiment.

Figure 14:
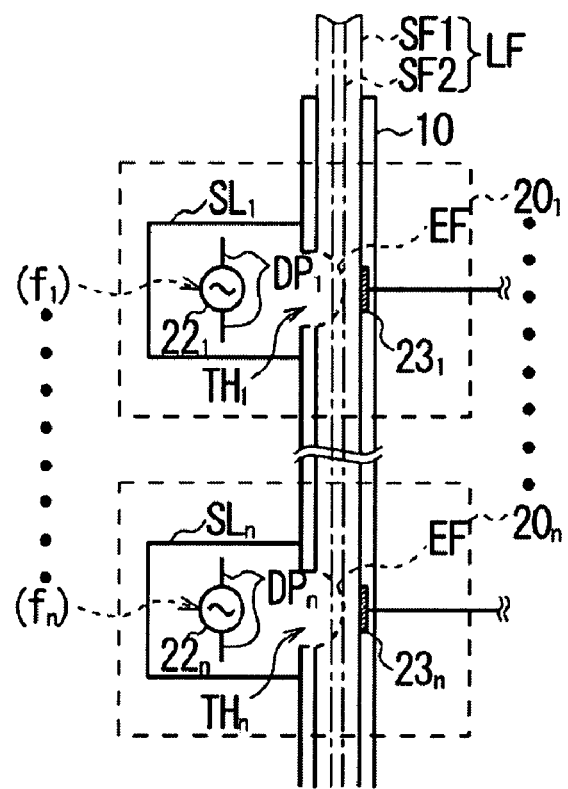
FIG. 14 is a schematic diagram illustrating a detection unit (2) according to another embodiment of the present invention.

Alternatively, the flow cytometer may include a detection unit as shown in FIG. 14 (the parts of FIG. 14 are designated by the same reference numerals and symbols as the corresponding parts of FIG. 5).

The electric field formation means of the detection unit (FIG. 14) generates a near field as the quasi-electrostatic field. In this case, the layer flow tube 10 has a plurality of pass-through holes $TH_1$ to $TH_n$ at certain intervals along the layer flow. Facing the pass-through holes $TH_1$ to $TH_n$, the elastic wave detection sections $23_1$ to $23_n$ are provided between the outer and inner walls of the layer flow tube 10. This detection unit also includes shields $SL_1$ to $SL_n$ on the outer wall of the layer flow tube 10, covering the pass-through holes $TH_1$ to $TH_n$. In a space (also referred to as a "shield interior space") between the inner wall of the shield and the outer wall of the layer flow tube, there are the sine wave signal output section 22 and the infinitesimal dipole DP connected to the sine wave signal output section.

In the detection unit (FIG. 14), when the sine wave signal output sections $22_1$ to $22_n$ apply the sine wave alternating voltage to the infinitesimal dipole $DP_1$ to $DP_n$, the quasi-electrostatic field dominant space (or the quasi-electrostatic field, which is dominant over the radiated electric field and the induction field) expands inside the shield interior space. In addition, part of the quasi-electrostatic field goes outside from the pass-through holes $TH_1$ to $TH_n$, producing a near field EF.

In this case, the thickness of the quasi-electrostatic field (near field) EF is substantially the same as the radius of the pass-through holes $TH_1$ to $TH_n$, even when the following condition is not satisfied for the frequency of the sine wave alternating voltage: in the detection target area, the intensity of the quasi-electrostatic field (which is in inverse proportion to the cube of the distance from the reference position) is stronger than the intensity of the induction field (which is in inverse proportion to the square of the distance from the reference position).

Figure 15:
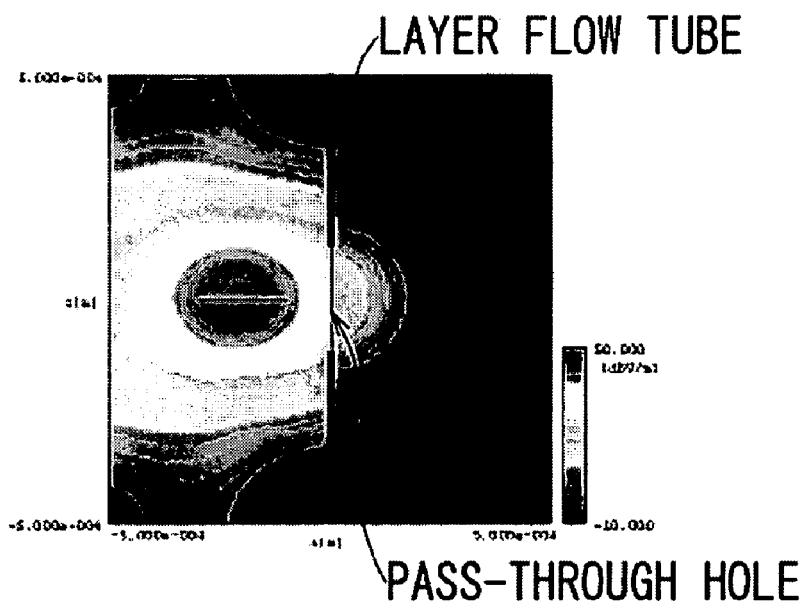
FIG. 15 is a schematic diagram illustrating the result of simulation regarding an electric field intensity distribution pattern (3)

FIG. 15 shows the result of simulation for one of the quasi-electrostatic fields (electrostatic field) generated around the marker detection sections $20_1$ to $20_n$. FIG. 15 is a cross sectional view of the layer flow tube in the horizontal direction (or a direction perpendicular to the layer flow). The condition of the simulation is the same as that of FIGS. 7 and 8. It is evident from FIG. 15 that the thickness of the generated quasi-electrostatic fields (electrostatic field) is substantially the same as the radius of the pass-through holes $TH_1$ to $TH_n$. By the way, the attached reference drawing 3 uses several colors to illustrate the distribution pattern of the electric field intensity of FIG. 15.

The detection unit (FIG. 14) may be more useful than the detection unit 3 (FIG. 5) because it is easy to select the frequency of the sine wave alternating voltage. Note that the frequency of the sine wave alternating voltage should be the same as the vibration frequency of the piezoelectric substance attached to the target sample and that the frequency (wavelength) of the sine wave alternating voltage should be longer than the pass-through holes. In addition, a corresponding elastic wave detection section should be inside the quasi-electrostatic field (near field) generated from the pass-through holes.

Figure 16:
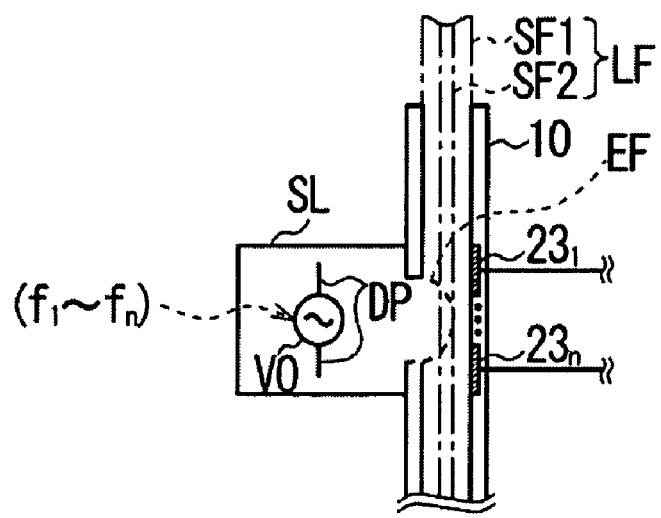
FIG. 16 is a schematic diagram illustrating a detection unit (3) according to another embodiment of the present invention.

Alternatively, a detection section (FIG. 16) can be applied (The parts of FIG. 16 have been designated by the same reference numerals and symbols as the corresponding parts of FIG. 14).

Figure 17:
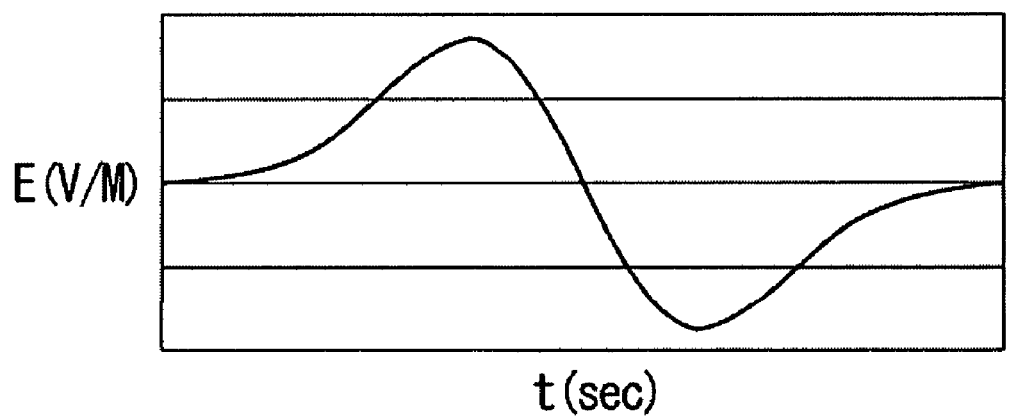
FIG. 17 is a schematic diagram illustrating a differential Gaussian pulse.

The configuration of detection section (FIG. 16) is almost the same as the detection unit (FIG. 14) except that: The detection section (FIG. 16) has one pass-through hole TH, one shield SL and one infinitesimal dipole DP; and the detection section (FIG. 16) has a plurality of elastic wave detection sections $23_1$ to $23_n$ facing the pass-through hole TH. In addition, instead of the sine wave signal output sections 22, the detection unit (FIG. 16) includes a voltage source VO that applies a voltage whose waveform is differential Gaussian pulse including various frequency components (FIG. 17).

In the detection unit (FIG. 16), when the voltage source VO applies the voltage of differential Gaussian pulse to the infinitesimal dipole DP, the quasi-electrostatic field is generated in the shield interior space and getting into the layer flow tube 10 through the pass-through hole TH, creating the electrostatic field (near field) EF. When the target sample with one or two piezoelectric substances passes through the electrostatic field, the piezoelectric substances vibrates in their unique vibration frequencies (due to the inverse piezoelectric effect) and the elastic wave detection sections $23_1$ to $23_n$ therefore detect the vibration as elastic wave. The corresponding IDT 32 (FIG. 9) of the elastic wave detection section extracts that elastic wave.

The detection unit (FIG. 16) may be more useful than the detection unit (FIG. 14) because it has less number of the shields SL and infinitesimal dipole DP than the detection unit (FIG. 14) and the layer flow tube 10 does not take much space. Note that the elastic wave detection sections $23_1$ to $23_n$ should be inside the quasi-electrostatic field (near field) generated from the pass-through holes TH.

Instead of the differential Gaussian pulse, the detection unit (FIG. 16) may use, as the various frequencies components of wave, surface transverse waves (STW), Rayleigh waves (Surface Acoustic Wave (SAW)), SH surface waves (BGS wave: Bleustein-Gulyaev-Simizu wave), Lamb waves, Surface-Skimming waves, Shear Horizontal (SH) bulk waves and the like.

Figure 18:
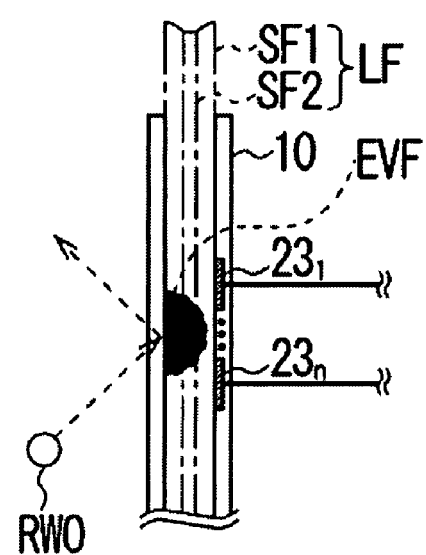
FIG. 18 is a schematic diagram illustrating a detection unit (4) according to another embodiment of the present invention.

Alternatively, a detection section (FIG. 18) can be applied (The parts of FIG. 18 have been designated by the same reference numerals and symbols as the corresponding parts of FIG. 16).

The configuration of detection section (FIG. 18) is almost the same as the detection unit (FIG. 16) except that it generates, instead of the electrostatic field (near field), an evanescent field inside the layer flow tube 10.

Instead of the pass-through hole TH, the shield SL and the infinitesimal dipole DP, the detection unit (FIG. 18) includes an electromagnetic wave emission source RWO that emits the electromagnetic wave including various frequency components to the outer wall of the layer flow tube 10 at a predetermined angle such that it is totally internally reflected from the outer wall.

After the electromagnetic wave, emitted by the electromagnetic wave emission source RWO, is totally reflected from the outer wall of the layer flow tube 10, the evanescent light, whose thickness is substantially the same as the wavelength of the electromagnetic wave, is generated and is getting into the layer flow tube 10, creating the evanescent field.

The detection unit (FIG. 18) may be more useful than the detection unit (FIG. 16) because it has less number of components than the detection unit (FIG. 16) and the layer flow tube 10 does not take much space. Note that the elastic wave detection sections $23_1$ to $23_n$ should be inside the evanescent field.

Figure 19:
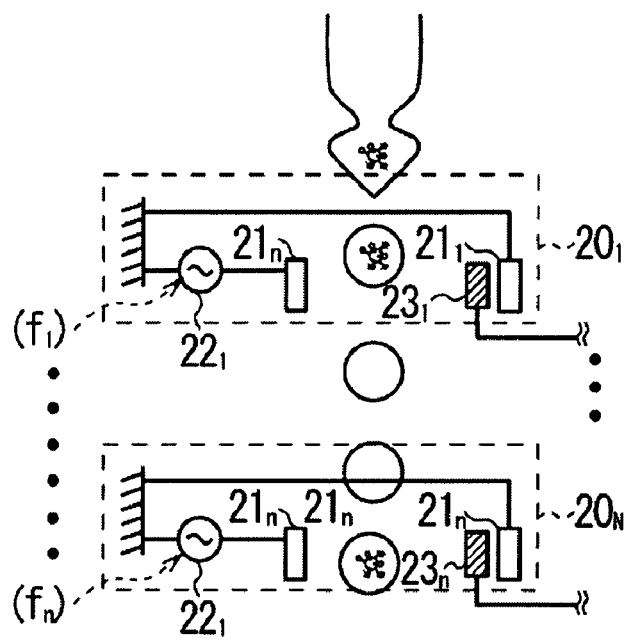
FIG. 19 is a schematic diagram illustrating a detection unit (5) according to another embodiment of the present invention.

Alternatively, a detection section (FIG. 19) can be applied (The parts of FIG. 19 have been designated by the same reference numerals and symbols as the corresponding parts of FIG. 5).

The detection unit (FIG. 19) detects the piezoelectric substance attached to the target sample inside a droplet broken off from the layer flow, while the detection unit 3 (FIG. 5) detects the piezoelectric substance attached to the target sample flowing in the sample flow (part of the layer flow). Accordingly, the detection unit (FIG. 19) can be downsized because it does not have the layer flow tube 10.

By the way, for ease of explanation, FIG. 19 illustrates the connection lines passing through the path of the droplets. However, in fact, those connection lines are placed at a predetermined position.

Figure 20:
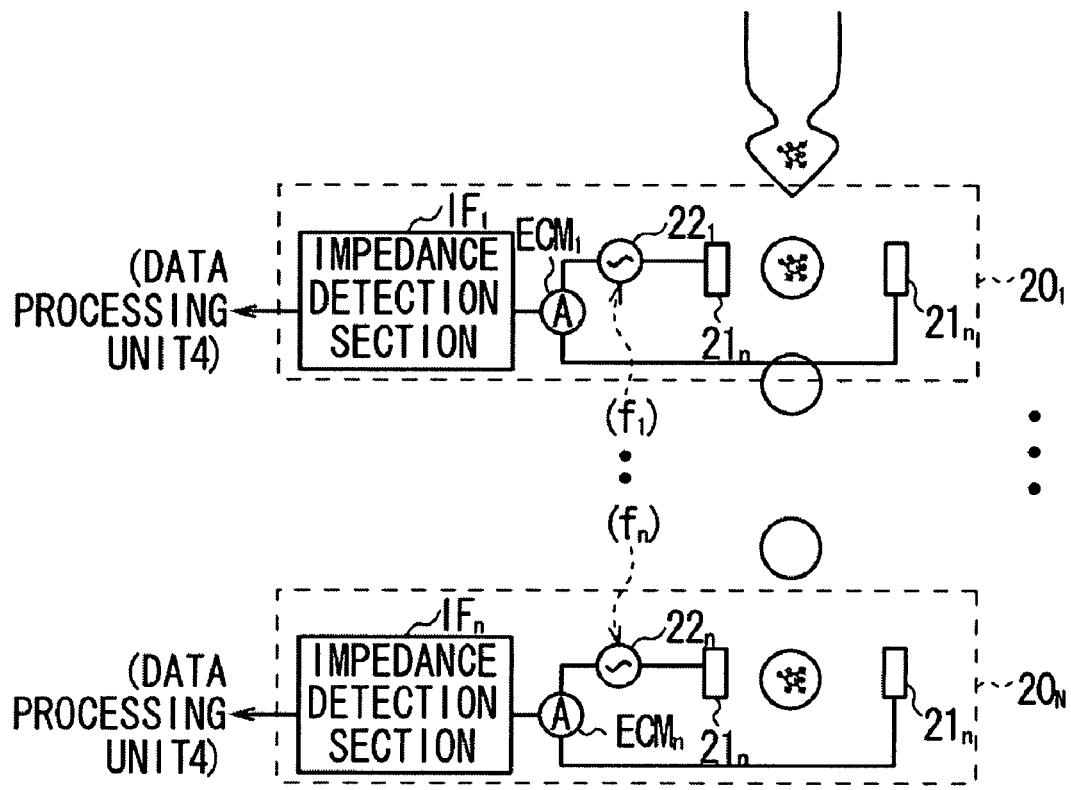
FIG. 20 is a schematic diagram illustrating a detection unit (6) according to another embodiment of the present invention.

Alternatively, a detection section (FIG. 20) can be applied (The parts of FIG. 20 have been designated by the same reference numerals and symbols as the corresponding parts of FIG. 19).

The detection unit (FIG. 20) is almost the same as the detection unit (FIG. 19) except that a detection means detects the change of impedance to detect the vibration of the piezoelectric substance attached to the target sample.

The detection unit (FIG. 20) includes: a plurality of parallel plane electrodes $21_1$ to $21_n$, which are spaced, along the layer flow, a certain distance from each other; sine wave signal output sections $22_1$ to $22_n$, connected to the parallel plane electrodes $21_1$ to $21_n$; ammeters $ECM_1$ to $ECM_n$, connected to the corresponding sine wave alternating voltage source and parallel plane electrode by lines; and impedance detection sections $IF_1$ to $IF_n$, connected to the ammeters $ECM_1$ to $ECM_n$.

By the way, for ease of explanation, FIG. 20 illustrates the connection lines passing through the path of the droplets. However, in fact, those connection lines are placed at a predetermined position.

For example, when the detection unit (FIG. 20) generates the quasi-electrostatic field dominant space (quasi-electrostatic field) the target sample labeled by two piezoelectric substances of different vibration frequencies flows in the sample flow SF2 (like FIG. 4). In this case, each parallel plane electrode 21 is generating the quasi-electrostatic field. When the target sample passes through one of the quasi-electrostatic fields whose frequency is the same as the vibration frequency of the piezoelectric substance attached to the target sample, that piezoelectric substance vibrates in its unique vibration frequency. The ammeters $ECM_1$ to $ECM_n$ therefore detect the change of current between the corresponding parallel plane electrodes.

The impedance detection sections $IF_1$ to $IF_n$ detect the change of impedance based on the measurement result of the ammeters $ECM_1$ to $ECM_n$ and a fixed voltage, generating a detection signal S1 to notify the data processing unit 4 of the fact that the a specific frequency of piezoelectric substance has been detected.

In that manner, the detection unit (FIG. 20) detects the change of impedance to identify the piezoelectric substance attached to the target sample.

Figure 21:
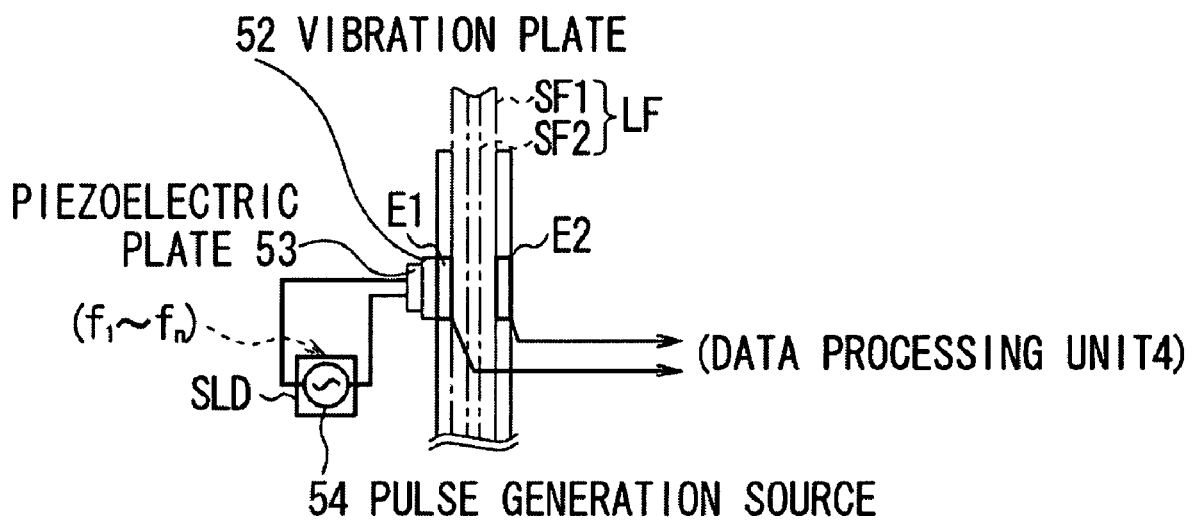
FIG. 21 is a schematic diagram illustrating a detection unit (7) according to another embodiment of the present invention.

Alternatively, a detection unit (FIG. 21) can be applied. The detection unit (FIG. 21) utilizes the piezoelectric effect to detect the piezoelectric substance attached to the target sample, while the detection unit 3 (FIG. 5) utilizes the inverse piezoelectric effect.

The detection unit (FIG. 21) includes: a pair of detection electrodes E1 and E2, which are placed between the outer and inner walls of the layer flow tube 10 and facing each other; a vibration plate 52, which is facing one of the detection electrodes E1 and E2 (the detection electrode E1, in this case) through the outer wall of the layer flow tube 10; an piezoelectric plate 53, attached to the vibration plate 52; and a pulse generation source 54, connected to the piezoelectric plate 53.

The pulse generation source 54, covered by a shield SLD, generates a mixed wave of different frequency components, such as differential Gaussian pulse. When the pulse generation source 54 supplies the mixed wave to the piezoelectric plate 53, the piezoelectric plate 53 is distorted by the mixed wave. This distortion is detected by the vibration plate 52 as vibration wave, conveying it into the layer flow tube 10.

When the target sample flows in the sample flow SF2, the piezoelectric substance attached to the target sample vibrates sympathetically with the vibration wave from the vibration plate 52, producing the quasi-electrostatic field (surface wave) due to the piezoelectric effect. The detection electrodes E1 and E2 detect this electric field and then generate a detection signal S2.

If a plurality of piezoelectric substances is attached to the target sample, the detection signal S2 may represent a plurality of surface waves corresponding to the plurality of piezoelectric substances of different vibration frequencies. Accordingly, the data processing unit 4 of the detection unit (FIG. 21) includes a signal processing section 44 that performs, after amplifying the detection signal S2, a Band Pass Filter (BPF) process to extract a surface wave corresponding to the vibration frequency of the attached piezoelectric substance and then performs an A/D conversion process.

Accordingly, the detection unit (FIG. 21) presents the same effect as the above detection unit 3.

Moreover, the detection units (FIGS. 5 and 13) may include components to cancel the expanding of the quasi-electrostatic field from the parallel plane electrodes $21_1$ to $21_n$ or the infinitesimal dipoles $DP_1$ to $DP_n$.

Figure 22:
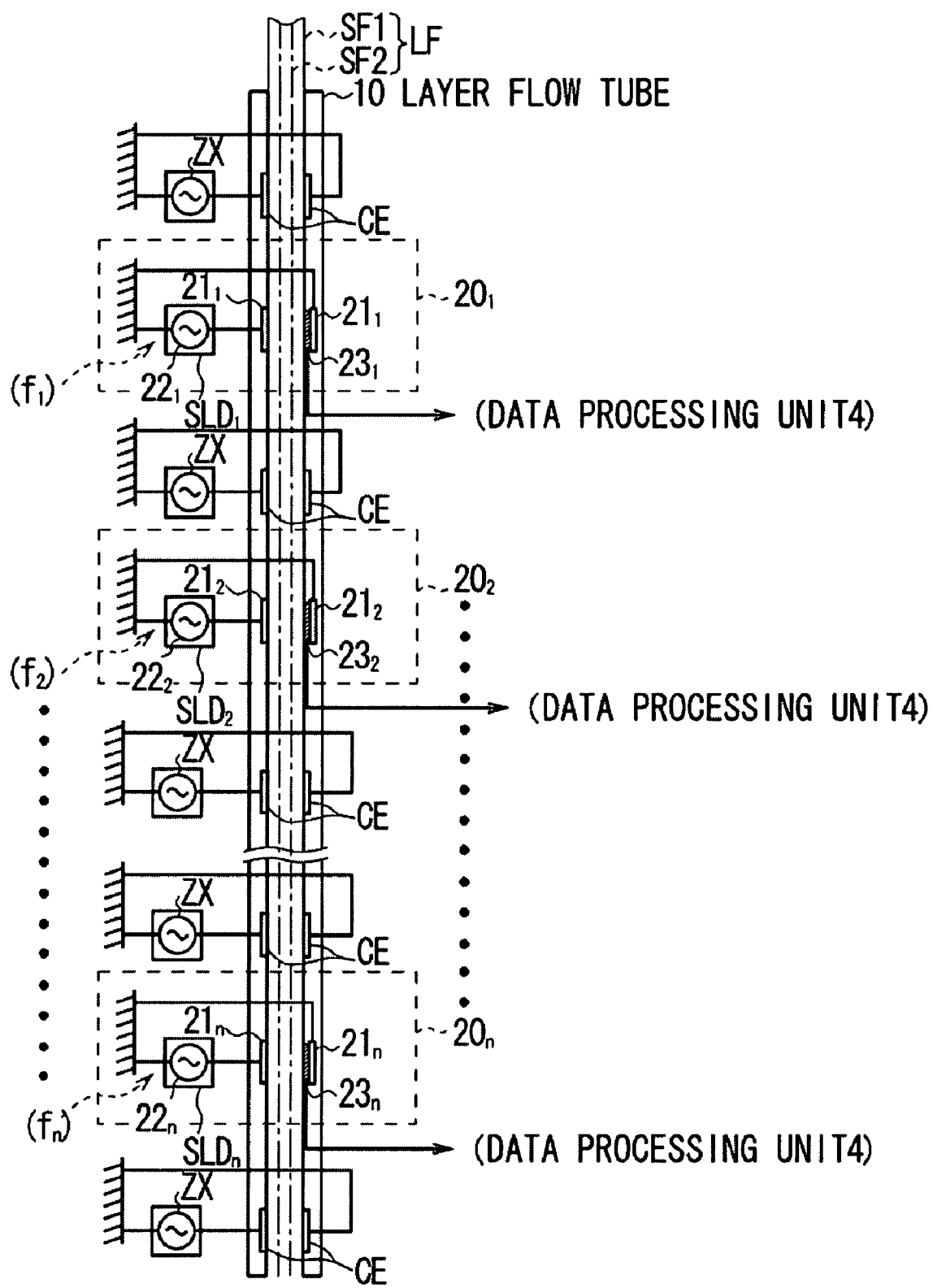
FIG. 22 is a schematic diagram illustrating a detection unit (8) according to another embodiment of the present invention.

Specifically, as shown in FIG. 22, the detection units (FIGS. 5 and 13) may include parallel plane electrodes (also referred to as "cancel electrodes") CE above and below the parallel plane electrodes 21x (x=1, 2, ... or n) to which the sine wave alternating voltage is applied. The cancel electrodes CE are to cancel the quasi-electrostatic field generated from the parallel plane electrodes 21x. The cancel electrodes CE are connected to an anti-phase voltage source ZX that applies a sine wave alternating voltage of predetermined amplitude, whose phase is opposite to the sine wave alternating voltage applied to the parallel plane electrodes 21x.

Generally, the coupling capacitance between the voltage-applied parallel plane electrodes 21x is inversely proportional to a distance between the electrodes and is proportional to the electric conductivity of the solution of the layer flow LF. Accordingly, that coupling capacitance C1 is represented as follows:

$$C1 = \frac{\sigma}{d1} \quad (14)$$

wherein "d1" is the distance between the electrodes and "σ" represents the electric conductivity of the solution of the layer flow.

On the other hand, the coupling capacitance between the voltage-applied parallel plane electrodes 21x and the cancel electrodes CE is inversely proportional to the distance between the parallel plane electrodes 21x and the cancel electrodes CE and is proportional to the relative permittivity of the material of the layer flow tube 10 and the frequency of the quasi-electrostatic field. Accordingly, that coupling capacitance C2 is represented as follows:

$$C2 = \frac{\omega \times \varepsilon pr}{d2} \quad (15)$$

wherein "d2" is the distance between the electrodes, "εpr" represents the relative permittivity of the material of the layer flow tube 10 and "ω" represents the frequency of the quasi-electrostatic field from the cancel electrodes CE.

The amplitude of the sine wave alternating voltage that the anti-phase voltage source ZX applies is determined such that the coupling capacitance C1 becomes equal to C2. As a result, the quasi-electrostatic fields generated from the cancel electrodes CE appropriately control the quasi-electrostatic fields generated from the parallel plane electrodes 21x.

Figure 23:
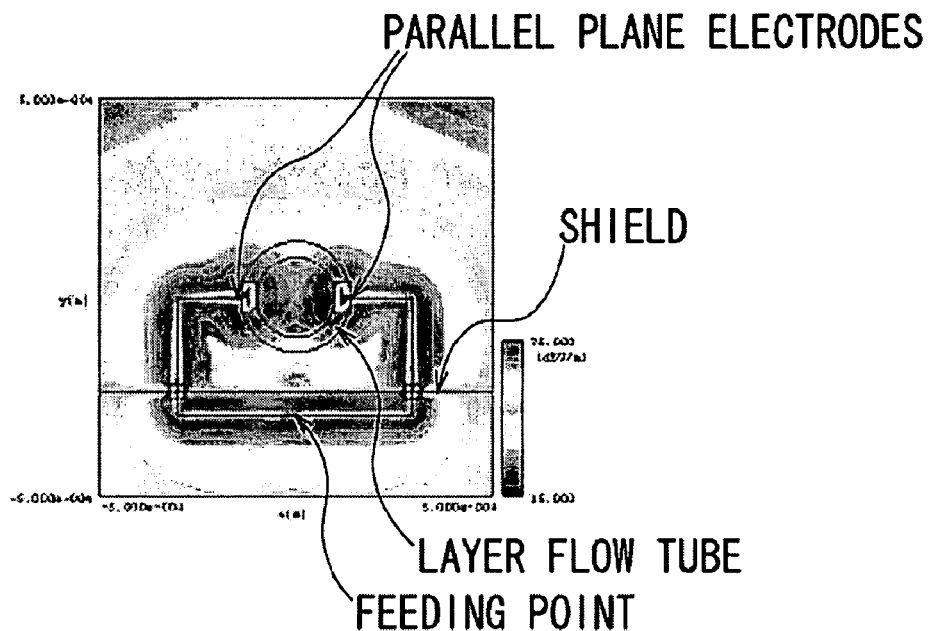
FIG. 23 is a schematic diagram illustrating the result of simulation regarding an electric field intensity distribution pattern (4)
Figure 24:
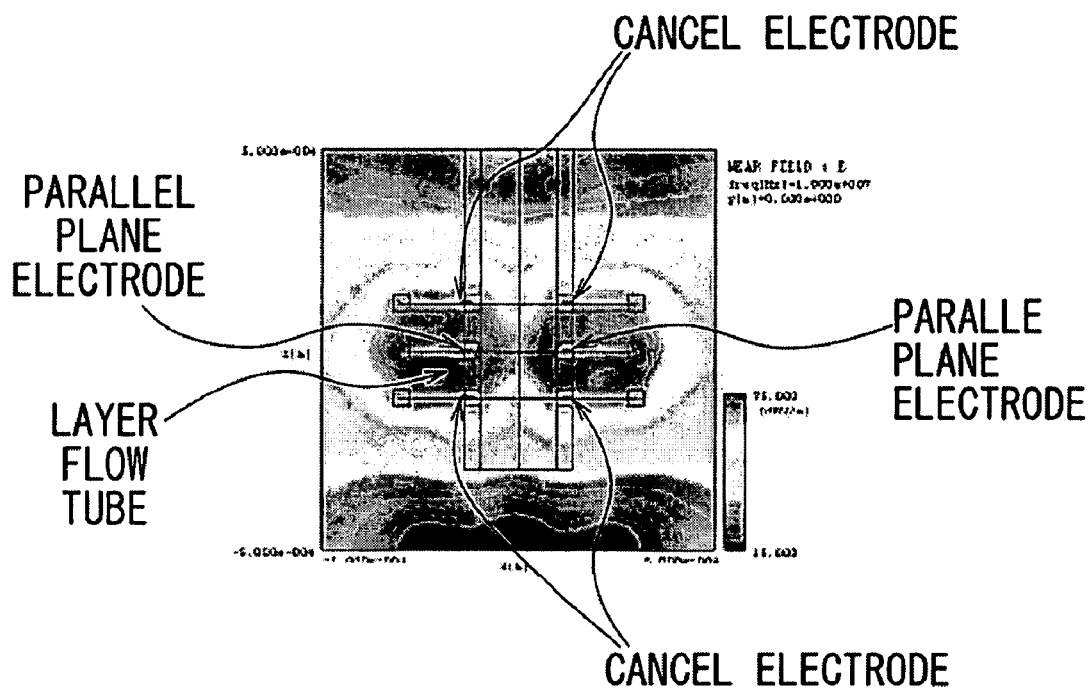
FIG. 24 is a schematic diagram illustrating the result of simulation regarding an electric field intensity distribution pattern (5)

FIGS. 23 and 24 show the result of the simulation regarding the quasi-electrostatic fields under the same condition as that of FIGS. 7 and 8: The detection unit (FIG. 5) has the cancel electrodes CE, which are spaced 120 μm from the parallel plane electrodes $21_1$ to $21_n$.

FIG. 23 is a cross sectional view of the layer flow tube in the horizontal direction (or a direction perpendicular to the layer flow). FIG. 24 is a cross sectional view of the layer flow tube in the vertical direction (or a direction parallel to the layer flow). By the way, the attached reference drawing 4 uses several colors to illustrate the distribution pattern of the electric field intensity of FIG. 23 while the attached reference drawing 5 uses several colors to illustrate the distribution pattern of the electric field intensity of FIG. 24.

Figure 25:
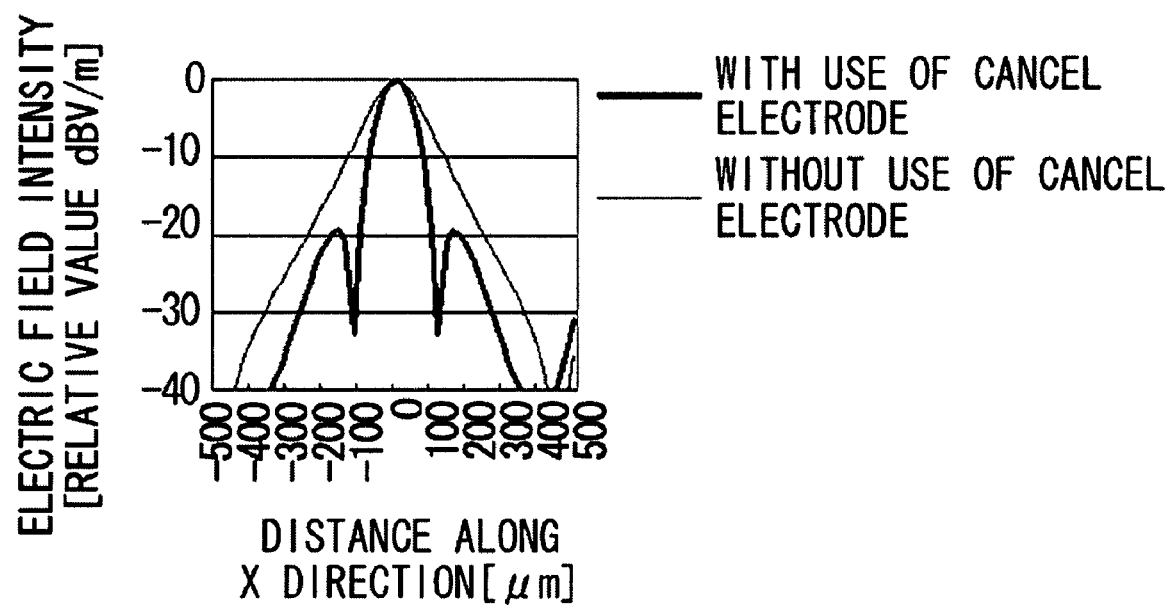
FIG. 25 is a schematic diagram illustrating how the intensity of electric fields changes around the center of a layer flow tube when using and not using a cancel electrode.

FIG. 25 is a graph illustrating the correlation between the distance from the center of the layer flow tube 10 and the electric field intensity when using and not using the cancel electrodes CE. It is evident from FIGS. 23 to 25 that: the area of the quasi-electrostatic field is limited around the parallel plane electrode 21x; the quasi-electrostatic field is formed only around the parallel plane electrode 21x. In this simulation, the amplitude of the sine wave alternating voltage applied to the cancel electrodes CE is 0.2 times that of the sine wave alternating voltage applied to the parallel plane electrode 21x.

In that manner, those canceling components control the expanse of the quasi-electrostatic field and therefore enable the apparatus to accurately detect the piezoelectric substances or markers.

Furthermore, in the above-noted embodiment, the elastic wave detection sections 23 are used as detection means for detecting vibration of particles (such as piezoelectric or electrostrictive substances). However, the present invention is not limited to this. The detection section may include a piezoelectric plate and a band pass filter connected to the plate, as a Surface Acoustic Wave (SAW) device to detect a specific elastic wave or the vibration of the particle.

Furthermore, in the above-noted embodiments, the flow cytometer 1 applies electric charge (for a certain type of sample) to the sample flow and then the charged droplet including the target sample are broken off from the flow by the deflection plates 5A and 5B with predetermined positive and negative voltages at the break off point. However, the present invention is not limited to this. Alternatively, a predetermined charge voltage may be applied to the sample flow while the voltage applied to the deflection plates 5A and 5B changes according to the type of the target samples so as to retrieve each sample.

However, that mechanism with the deflection plates 5A and 5B may not be applied to: the detection units (FIGS. 19 and 20), which detects directly from the droplets, and the detection unit (FIG. 21), which utilizes the piezoelectric effect to detect the piezoelectric substance attached to the target sample.

The method according to an embodiment of the present invention can be applied to medicine production.

It should be understood by those skilled in the art that various modifications, combinations, sub-combinations and alterations may occur depending on design requirements and other factors insofar as they are within the scope of the appended claims or the equivalents thereof.

What is claimed is:

1. A marker detection apparatus for detecting a marker attached to a target sample from samples flowing in a sample flow, the marker detection apparatus comprising:

an electric field formation section that forms a quasi-electrostatic field in a path of the sample flow; and a detection section that detects, when the target sample labeled by the marker that is a particle made from a piezoelectric or electrostrictive substance of a unique vibration frequency gets into the quasi-electrostatic field, the vibration of the particle.

2. The marker detection apparatus according to claim 1, wherein:

a plurality of units is provided along the sample flow to detect a plurality of particles of different vibration frequencies, each of the units including a pair of the electric field formation section and the detection section; and the detection sections are spaced a certain distance from each other such that each of the detection sections is not affected by the electric field formation sections other than the corresponding electric field formation section.

3. The marker detection apparatus according to claim 1, wherein
the electric field formation section includes:
first parallel plane electrodes outside the sample flow, the first parallel plane electrodes facing each other through the sample flow;
second and third parallel plane electrodes provided above and below the first parallel plane electrodes outside the sample flow, the second and third parallel plane electrodes facing each other through the sample flow;
a first output section that supplies, when the quasi-electrostatic field generated around the first parallel plane electrode is within an area including a cross section of the sample flow, to the first parallel plane electrodes a signal of a certain frequency that makes the intensity of the quasi-electrostatic field stronger than an induction field in the area; and
a second output section that supplies to the second and third parallel plane electrodes an anti-phase signal whose phase is opposite to the signal, wherein
an amplitude of the anti-phase signal is determined such that the coupling capacitance between the first parallel plane electrodes becomes equal to the coupling capacitance between the first parallel plane electrode and the second and third parallel plane electrodes.

4. The marker detection apparatus according to claim 1, wherein
the electric field formation section includes:
an electric field generation source outside the sample flow;
a shield covering the electric field generation source; and
a hole passing through the shield, wherein
a diameter of the hole is larger than a distance from the electric field generation source to the rim of a sheath flow flowing outside the sample flow.

5. The marker detection apparatus according to claim 1, further comprising:
a tube surrounding the sample flow; and
an emission source that emits an electromagnetic wave to an outer wall of the tube at a predetermined angle such that the electromagnetic wave is totally reflected from the outer wall, wherein
the wavelength of the electromagnetic wave is determined such that an evanescent field generated as a result of emitting the electromagnetic wave to the outer wall passes through the outer wall and covers the sample flow and the detection section.

6. The marker detection apparatus according to claim 1, wherein:
the electric field formation section forms the quasi-electrostatic field in a path of droplets broken off from the sample flow; and
the detection section detects change of impedance of the quasi-electrostatic field to detect the vibration of the particle when the particle attached to the target sample in the droplet gets into the quasi-electrostatic field.

7. The marker detection apparatus according to claim 1, wherein
the electric field formation section includes:
an electric field generation source outside the sample flow; and
an output section that supplies to the electric field generation source a signal of a certain frequency that makes the intensity of the quasi-electrostatic field stronger than an induction field when the quasi-electrostatic field generated around the electric field generation source is within an area including a cross section of the sample flow.

8. The marker detection apparatus according to claim 7, wherein
the electric field formation section includes a nonconducting tube that surrounds the sample flow, wherein the electric field generation source and the detection section are placed between the inner and outer walls of the tube.

9. The marker detection apparatus according to claim 7, wherein:
the detection section includes:
a piezoelectric plate; and
an Inter Digital Transducer (IDT) provided on the surface of the piezoelectric plate, wherein
the material of the piezoelectric plate and the shape of the IDT are determined such that the frequency of the signal output from the output section becomes equal to the center frequency of the IDT.

* * * * *